United States Patent
Danz et al.

(10) Patent No.: US 10,263,196 B2
(45) Date of Patent: Apr. 16, 2019

(54) ORGANIC MOLECULES FOR USE IN OPTOELECTRONIC DEVICES

(71) Applicant: CYNORA GMBH, Bruchsal (DE)

(72) Inventors: Michael Danz, Eggenstein-Leopoldshafen (DE); Daniel Zink, Bruchsal (DE)

(73) Assignee: CYNORA GMBH, Bruchsal (DE)

(*) Notice: Subject to any disclaimer, the term of this patent is extended or adjusted under 35 U.S.C. 154(b) by 0 days.

(21) Appl. No.: 15/541,590

(22) PCT Filed: Jul. 4, 2016

(86) PCT No.: PCT/EP2016/065724
§ 371 (c)(1),
(2) Date: Jul. 5, 2017

(87) PCT Pub. No.: WO2017/005699
PCT Pub. Date: Jan. 12, 2017

(65) Prior Publication Data
US 2018/0026202 A1    Jan. 25, 2018

(30) Foreign Application Priority Data

Jul. 3, 2015 (EP) .................................. 15175358
Dec. 17, 2015 (EP) .................................. 15200813
May 9, 2016 (EP) .................................. 16168821

(51) Int. Cl.
C07F 7/08      (2006.01)
C09K 11/06     (2006.01)
(Continued)

(52) U.S. Cl.
CPC ........ H01L 51/0072 (2013.01); C07D 209/08 (2013.01); C07D 209/56 (2013.01);
(Continued)

(58) Field of Classification Search
CPC .. C07D 209/08; C07D 209/80; C07D 209/82; C07D 209/86; C07D 209/88;
(Continued)

(56) References Cited

U.S. PATENT DOCUMENTS

2014/0131686 A1    5/2014  Kawakami et al.
2017/0186973 A1*   6/2017  Ren .................. H01L 51/0072

FOREIGN PATENT DOCUMENTS

WO    WO2014146752 A1    9/2014
WO    PCT/EP2016/065724   10/2016

OTHER PUBLICATIONS

S. Gong et al., "Simple CBP Isomers with High Triplet Energies for Highly Efficient Blue Electrophosphorescence," Journals of Materials Chemistry, Jan. 1, 2012, pp. 2894-2899, vol. 22.
(Continued)

*Primary Examiner* — Daniel P Shook
(74) *Attorney, Agent, or Firm* — Ryan, Mason & Lewis, LLP

(57) ABSTRACT

The invention relates to an organic molecule having precisely two units of formula I linked to one another via a single bond or a bridge Y Formula I (Continued)

where
Y=a divalent group;
X=at each occurrence identically or differently CN and $CF_3$;
D=chemical unit having a structure of the formula I-1:

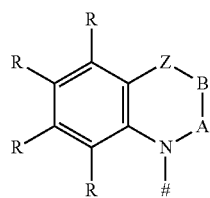

Formula I-1 where
=attachment point of the unit of formula I-1 to the structure of formula I;
A and B=independently of one another are selected from the group consisting of $CRR^1$, CR, NR, N, there being a single or double bond between A and B and a single or double bond between B and Z;
Z=a direct bond or a divalent organic bridge which is a substituted or unsubstituted C1-C9-alkylene, C2-C8-alkenylene, C2-C8-alkynylene or arylene group or a combination thereof, —$CRR^1$—, —C=$CRR^1$, —C=NR, —NR—, —O—, —$SiRR^1$—, —S—, —S(O)—, —S$(O)_2$—, O-interrupted substituted or unsubstituted C1-C9-alkylene, C2-C8-alkenylene, C2-C8-alkynylene or arylene group, phenyl units or substituted phenyl units.

20 Claims, 8 Drawing Sheets

(51) Int. Cl.

| | | |
|---|---|---|
| H01L 51/00 | (2006.01) | |
| H01L 51/50 | (2006.01) | |
| C07D 209/08 | (2006.01) | |
| C07D 209/56 | (2006.01) | |
| C07D 209/80 | (2006.01) | |
| C07D 209/82 | (2006.01) | |
| C07D 209/86 | (2006.01) | |
| C07D 209/88 | (2006.01) | |
| C07D 215/06 | (2006.01) | |
| C07D 219/08 | (2006.01) | |
| C07D 219/14 | (2006.01) | |
| C07D 241/48 | (2006.01) | |
| C07D 265/38 | (2006.01) | |
| C07D 279/02 | (2006.01) | |
| C07D 279/22 | (2006.01) | |
| C07D 279/26 | (2006.01) | |
| C07D 279/34 | (2006.01) | |
| C07D 403/04 | (2006.01) | |
| C07D 417/10 | (2006.01) | |
| C07D 487/04 | (2006.01) | |
| C07D 409/10 | (2006.01) | |
| C07D 409/14 | (2006.01) | |
| C07D 417/14 | (2006.01) | |

(52) U.S. Cl.
CPC ......... *C07D 209/80* (2013.01); *C07D 209/82* (2013.01); *C07D 209/86* (2013.01); *C07D 209/88* (2013.01); *C07D 215/06* (2013.01); *C07D 219/08* (2013.01); *C07D 219/14* (2013.01); *C07D 241/48* (2013.01); *C07D 265/38* (2013.01); *C07D 279/02* (2013.01); *C07D 279/22* (2013.01); *C07D 279/26* (2013.01); *C07D 279/34* (2013.01); *C07D 403/04* (2013.01); *C07D 409/10* (2013.01); *C07D 409/14* (2013.01); *C07D 417/10* (2013.01); *C07D 417/14* (2013.01); *C07D 487/04* (2013.01); *C07F 7/0816* (2013.01); *C09K 11/06* (2013.01); *H01L 51/0052* (2013.01); *H01L 51/0061* (2013.01); *H01L 51/0068* (2013.01); *H01L 51/0071* (2013.01); *H01L 51/0094* (2013.01); *C09K 2211/1018* (2013.01); *H01L 51/001* (2013.01); *H01L 51/0003* (2013.01); *H01L 51/5004* (2013.01); *H01L 51/5012* (2013.01); *H01L 51/5024* (2013.01); *H01L 51/5072* (2013.01); *H01L 51/5088* (2013.01); *H01L 51/5096* (2013.01); *H01L 2251/552* (2013.01); *Y02E 10/549* (2013.01); *Y02P 70/521* (2015.11)

(58) Field of Classification Search
CPC .. C07D 215/06; C07D 219/14; C07D 265/38; C07D 279/22; C07D 487/04; H01L 51/0072
See application file for complete search history.

(56) References Cited

OTHER PUBLICATIONS

N.R. Madadi et al., "Synthesis and Anti-Proliferative Activity of Aromatic Substituted 5-((1-benzyl-1H-indol-3-yl) methylene)-1,3-dimethylpyrimidine-2,4,6(1H,3H,5H)-Trione Analogs Against Human Tumor Cell Lines," Bioorganic & Medicinal Chemistry Letters, Dec. 9, 2013, pp. 601-603, vol. 24.

* cited by examiner

ORGANIC MOLECULES FOR USE IN OPTOELECTRONIC DEVICES

CROSS-REFERENCE TO RELATED APPLICATIONS

This application claims priority to International Application No. PCT/EP2016/065724, filed Jul. 4, 2016, which claims priority to European Patent Application No. 15175358.9 filed Jul. 3, 2015 and European Patent Application No. 15200813.2 filed Dec. 17, 2015, and European Patent Application No. 16168821.3 filed May 9, 2016, the disclosures of which are incorporated by reference herein in their entireties.

FIELD OF INVENTION

The invention relates to purely organic molecules and to the use thereof in organic light-emitting diodes (OLEDs) and in other organic optoelectronic devices.

BACKGROUND

A feature or organic optoelectronic devices is either that electrical energy is converted into photons (organic light-emitting diodes, OLEDs, or light-emitting electrochemical cells, LEECs) or that the opposite process occurs (organic photovoltaics, OPVs). It is important here that these processes run as efficiently as possible. For the sector of OLEDs, therefore, it is necessary ideally to use materials having maximum photoluminescent quantum yield. Limited efficiencies in OLED materials can be improved by using efficient materials which exhibit thermally activated delayed fluorescence (TADF), since, in contrast to purely fluorescent materials, up to 100% of the excitons, rather than 25% of the excitons formed in an OLED, can be utilized. The triplet excitons formed can also in this case be converted into singlet excitons, a state from which photons can then be emitted. A precondition for such thermal repopulation is a low energetic distance between the lowest excited singlet level ($S_1$) and triplet level ($T_1$). This may be achieved, for example, through use of copper(I) complexes (in this regard see, for example: H. Yersin, U. Monkowius, T. Fischer, T. Hofbeck, WO 2010/149748 A1) or else by means of purely organic materials (in this regard see, for example: Q. Zhang et al., *J. Am. Chem. Soc.* 2012, 134, 14706, WO 2013161437 A1).

There is also a large demand for new materials, as for example for deep-blue TADF OLEDs. Existing blue TADF materials often exhibit high exciton lifetimes, which are bad for efficient and long-lived OLEDs. Besides the aforementioned properties of the materials, their availability is also relevant with regard to commercialization. This includes the availability of synthesis building blocks, and also the cost and convenience of the actual synthesis of the functional material, particularly including the purification of this material.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
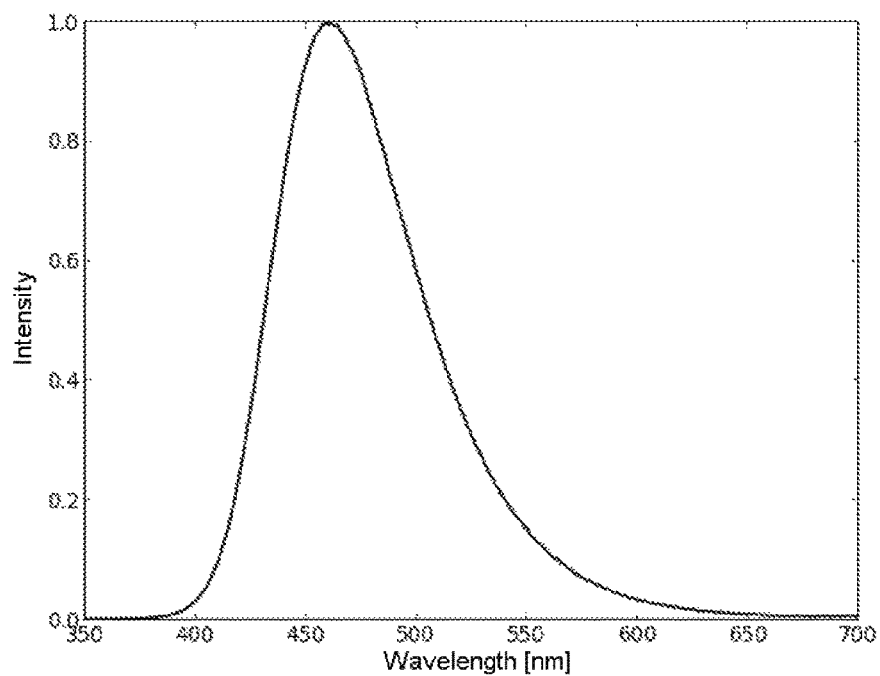
FIG. 1 is a film emission of product 1 (10% in PMMA).

Exemplary embodiments of the invention will now be discussed in further detail. This invention may, however, be embodied in many different forms and should not be construed as limited to the embodiments set forth herein.

The invention provides a new class of molecules which contain exactly two units of formula I, these being a first unit of formula I and a second unit of formula I.

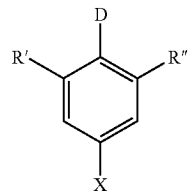

Formula I

The two units of formula I are linked to one another via a single bond (so that the phenyl rings are bonded directly to one another via a single bond) or are linked to one another via a bridge Y formed by R' and/or R", the single bond or the bridge Y being formed alternatively via R' of the first unit of formula I and R' of the second unit of formula I or via R" of the first unit of formula I and R' of the second unit of formula I or via R' of the first unit of formula I and R" of the second unit of formula I or via R" of the first unit of formula I and R" of the second unit of formula I. This means that the bridge Y links to the position R' and/or R" or, respectively, the single bond is present between two positions R' and/or R" of two units of formula I.

In formula I
Y=an arbitrary divalent chemical group;
X=at each occurrence identically or differently CN or $CF_3$;
D=chemical unit having a structure of the formula I-1:

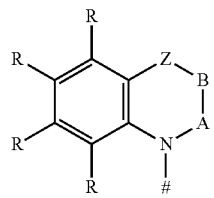

Formula I-1 where

=attachment point of the unit of formula I-1 to the structure of formula I;

A and B=independently of one another selected from the group consisting of $CRR^1$, CR, NR, N, there being a single or double bond between A and B and a single or double bond between B and Z;

Z=a direct bond or a divalent organic bridge which is a substituted or unsubstituted C1-C9-alkylene, C2-C8-alkenylene, C2-C8-alkynylene or arylene group or a combination thereof, —$CRR^1$—, —C=$CRR^1$, —C=NR, —NR—, —O—, —$SiRR^1$—, —S—, —S(O)—, —S(O)$_2$—, O-interrupted substituted or unsubstituted C1-C9-alkylene, C2-C8-alkenylene, C2-C8-alkynylene or arylene group, phenyl units or substituted phenyl units;

where each R and $R^1$, identically or differently at each occurrence, is H, deuterium, azide ($N_3^-$), F, Cl, Br, I, $N(R^2)_2$, CN, $CF_3$, $NO_2$, OH, COOH, $COOR^2$, $CO(NR^2)_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which in each case may be substituted by one or more radicals $R^2$, it being possible for one or more non-adjacent $CH_2$ groups to be replaced by $R^2C=CR^2$, C≡C, $Si(R^2)_2$, $Ge(R^2)_2$, $Sn(R^2)_2$, C=O, C=S, C=Se, C=$NR^2$, P(=O)($R^2$), SO, $SO_2$, $NR^2$, O, S or $CONR^2$, and it being possible for one or more H atoms to be replaced by deuterium, F, Cl, Br, I, CN, $CF_3$ or $NO_2$, or is an aromatic or heteroaromatic ring system having 5 to 60 aromatic ring atoms, it being possible for this ring system to be substituted in each case by one or more radicals $R^2$, or is an aryloxy or heteroaryloxy group having 5 to 60 aromatic ring atoms, it being possible for this group to be substituted by one or more radicals $R^2$, or is a diarylamino group, diheteroarylamino group or arylheteroarylamino group having 10 to 40 aromatic ring atoms, it being possible for this group to be substituted by one or more radicals $R^2$, or is a combination of these systems, or is a crosslinkable unit QE which may be crosslinked by acid-catalytic, thermal or UV crosslinking methods in the presence or absence of a photoinitiator or by microwave radiation; two or more of these substituents R and $R^1$ may form with one another a mono- or polycyclic, aliphatic, aromatic and/or benzo-fused ring system;

$R^2$, identically or differently at each occurrence, is H, deuterium, F, Cl, Br, I, $N(R^3)_2$, CN, $CF_3$, $NO_2$, OH, COOH, $COOR^3$, $CO(NR^3)_2$, $Si(R^3)_3$, $B(OR^3)_2$, $C(=O)R^3$, P(=O)($R^3$)$_2$, $S(=O)R^3$, $S(=O)_2R^3$, $OSO_2R^3$, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which may be substituted in each case by one or more radicals $R^3$, it being possible for one or more non-adjacent $CH_2$ groups to be replaced by $R^3C=CR^3$, C≡C, $Si(R^3)_2$, $Ge(R^3)_2$, $Sn(R^3)_2$, C=O, C=S, C=Se, C=$NR^3$, P(=O)($R^3$), SO, $SO_2$, $NR^3$, O, S or $CONR^3$, and it being possible for one or more H atoms to be replaced by deuterium, F, Cl, Br, I, CN, $CF_3$ or $NO_2$, or is an aromatic or heteroaromatic ring system having 5 to 60 aromatic ring atoms, it being possible for this system to be substituted in each case by one or more radicals $R^3$, or is an aryloxy or heteroaryloxy group having 5 to 60 aromatic ring atoms, it being possible for this group to be substituted by one or more radicals $R^3$, or is a diarylamino group, diheteroarylamino group or arylheteroarylamino group having 10 to 40 aromatic ring atoms, it being possible for this group to be substituted by one or more radicals $R^3$, or is a combination of these systems; two or more of these substituents $R^2$ may form with one another a mono- or polycyclic, aliphatic, aromatic and/or benzo-fused ring system;

$R^3$, identically or differently at each occurrence, is H, deuterium, F, $CF_3$ or an aliphatic, aromatic and/or heteroaromatic hydrocarbon radical having 1 to 20 C atoms, in which also one or more H atoms may be replaced by F or $CF_3$; two or more substituents $R^3$ may form with one another a mono- or polycyclic, aliphatic ring system;

R'=attachment position for the second unit of the formula I or selected from the group consisting of Y, H, $N(R^4)_2$, $OR^4$, a linear alkyl or alkoxy group having 1 to 40 C atoms or a branched or cyclic alkyl or alkoxy group having 3 to 40 C atoms, it being possible for this group to be substituted in each case by one or more radicals $R^4$, and an aromatic or heteroaromatic ring system having 5 to 60 aromatic ring atoms, it being possible for this system to be substituted in each case by one or more radicals $R^4$;

R''=attachment position for the second unit of the formula I or selected from the group consisting of Y, $N(R^4)_2$, $OR^4$, a linear alkyl or alkoxy group having 1 to 40 C atoms or a branched or cyclic alkyl or alkoxy group having 3 to 40 C atoms, it being possible for this group to be substituted in each case by one or more radicals $R^4$, and an aromatic or heteroaromatic ring system having 5 to 60 aromatic ring atoms, it being possible for this system to be substituted in each case by one or more radicals $R^4$;

with the proviso that if R' is Y, R'' is not Y, and, if R'' is Y, R' is not Y;

and with the proviso that if R' is the attachment position for the second unit of the formula I, R'' is not the attachment position for the second unit of the formula I, and, if R'' is the attachment position for the second unit of the formula I, R' is not the attachment position for the second unit of the formula I;

$R^4$, identically or differently at each occurrence, is H, deuterium, $N(R^5)_2$, $Si(R^5)_3$, a linear alkyl, alkoxy or thioalkoxy group having 1 to 40 C atoms or a branched or cyclic alkyl, alkoxy or thioalkoxy group having 3 to 40 C atoms, it being possible for this group to be substituted in each case by one or more radicals $R^5$, or is an aromatic or heteroaromatic ring system having 5 to 60 aromatic ring atoms, it being possible for this system to be substituted in each case by one or more radicals $R^5$, or is an aryloxy or heteroaryloxy group having 5 to 60 aromatic ring atoms, it being possible for this group to be substituted by one or more radicals $R^5$, or is a diarylamino group, diheteroarylamino group or arylheteroarylamino group having 10 to 40 aromatic ring atoms, it being possible for this group to be substituted by one or more radicals $R^5$, or is a combination of these systems; two or more of these substituents $R^5$ may also form with one another a mono- or polycyclic, aliphatic, aromatic and/or benzo-fused ring system;

$R^5$, identically or differently at each occurrence, is H, deuterium or an aliphatic, aromatic and/or heteroaromatic hydrocarbon radical having 1 to 20 C atoms; two or more substituents $R^5$ may also form with one another a mono- or polycyclic, aliphatic ring system.

In a further embodiment, R' is H and R'' is the attachment point for the second unit of the formula I or is Y.

In a further embodiment, R' is selected from the group consisting of Y, H, $N(R^4)_2$, $OR^4$, a linear alkyl or alkoxy group having 1 to 40 C atoms or a branched or cyclic alkyl or alkoxy group having 3 to 40 C atoms, it being possible for this group to be substituted in each case by one or more radicals R⁴, and of an aromatic or heteroaromatic ring system having 5 to 60 aromatic ring atoms, it being possible for this ring system to be substituted in each case by one or more radicals R⁴, and R" is selected from the group consisting of Y, N(R⁴)₂, OR⁴, a linear alkyl or alkoxy group having 1 to 40 C atoms or a branched or cyclic alkyl or alkoxy group having 3 to 40 C atoms, it being possible for this group to be substituted in each case by one or more radicals R⁴, and of an aromatic or heteroaromatic ring system having 5 to 60 aromatic ring atoms, it being possible for this ring system to be substituted in each case by one or more radicals R⁴; with the proviso that if R' is Y, R" is not Y, and, if R" is Y, R' is not Y.

In one embodiment, R'=attachment position for the second unit of the formula I or selected from the group consisting of Y, H, N(R⁴)₂, OR⁴, thiophene which may be substituted by one or more radicals R⁴, a linear alkyl or alkoxy group having 1 to 40 C atoms or a branched or cyclic alkyl or alkoxy group having 3 to 40 C atoms, it being possible for this group to be substituted in each case by one or more radicals R⁴, and an aromatic ring system having 5 to 60 aromatic ring atoms, it being possible for this system to be substituted by one or more radicals R⁴;

and R"=attachment position for the second unit of the formula I or selected from the group consisting of Y, N(R⁴)₂, OR⁴, thiophene which may be substituted by one or more radicals R⁴, a linear alkyl or alkoxy group having 1 to 40 C atoms or a branched or cyclic alkyl or alkoxy group having 3 to 40 C atoms, it being possible for this group to be substituted in each case by one or more radicals R⁴, and an aromatic ring system having 5 to 60 aromatic ring atoms, it being possible for this system to be substituted by one or more radicals R⁴;

with the proviso that if R' is Y, R" is not Y, and, if R" is Y, R' is not Y;

and with the proviso that if R' is the attachment position for the second unit of the formula I, R" is not the attachment position for the second unit of the formula I, and, if R" is the attachment position for the second unit of the formula I, R' is not the attachment position for the second unit of the formula I;

where Y and R⁴ are as defined above.

In one embodiment, R'=attachment position for the second unit of the formula I or selected from the group consisting of Y, H, N(R⁴)₂, OR⁴, a linear alkyl or alkoxy group having 1 to 40 C atoms or a branched or cyclic alkyl or alkoxy group having 3 to 40 C atoms, it being possible for this group to be substituted in each case by one or more radicals R⁴, and an aromatic or heteroaromatic ring system having 5 to 60 aromatic ring atoms, it being possible for this system to be substituted in each case by one or more radicals R⁴;

and R"=attachment position for the second unit of the formula I or selected from the group consisting of Y, N(R⁴)₂, OR⁴, a linear alkyl or alkoxy group having 1 to 40 C atoms or a branched or cyclic alkyl or alkoxy group having 3 to 40 C atoms, it being possible for this group to be substituted in each case by one or more radicals R⁴, and an aromatic or heteroaromatic ring system having 5 to 60 aromatic ring atoms, it being possible for this system to be substituted in each case by one or more radicals R⁴;

with the proviso that the heteroaromatic ring system is not an N-heteroaromatic;

and with the proviso that if R' is Y, R" is not Y, and, if R" is Y, R' is not Y;

and with the proviso that if R' is the attachment position for the second unit of the formula I, R" is not the attachment position for the second unit of the formula I, and, if R" is the attachment position for the second unit of the formula I, R' is not the attachment position for the second unit of the formula I;

where Y and R⁴ are as defined above.

An aryl group in the sense of this invention contains 6 to 60 aromatic ring atoms; a heteroaryl group in the sense of this invention contains 5 to 60 aromatic ring atoms, of which at least one represents a heteroatom. The heteroatoms are preferably N, O, and/or S. This is the fundamental definition. If other preferences are stated in the description of the present invention, in relation to the number of aromatic ring atoms or of heteroatoms present, for example, then these apply.

An aryl group or heteroaryl group here, respectively, is a simple aromatic ring, i.e. benzene, or a simple heteroaromatic ring, such as pyridine, pyrimidine or thiophene, or a heteroaromatic polycyclic system, as for example phenanthrene, quinoline or carbazole. A condensed (fused) aromatic or heteroaromatic polycyclic system in the sense of the present patent application consists of two or more simple aromatic and/or heteroaromatic rings which are fused with one another.

An aryl or heteroaryl group, which may be substituted in each case by the radicals stated above and may be linked via any desired positions on the aromatic or heteroaromatic moiety is understood in particular to refer to groups derived from benzene, naphthaline, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3, 4-tetrazine, purine, pteridine, indolizine and benzothiadiazole or combinations of these groups.

A cyclic alkyl, alkoxy or thioalkoxy group in the sense of this invention refers to a monocyclic, bicyclic or polycyclic group.

For the purposes of the present invention, a $C_1$- to $C_{40}$-alkyl group, in which individual H atoms or $CH_2$ groups may also be substituted by the groups stated above, refers for example to the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyl-n- hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyl-n-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl-. An alkenyl group refers for example to ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group refers for example to ethynyl, propynyl, butynyl, pentynyl, hexynyl, heptynyl or octynyl. A $C_1$- to $C_{40}$-alkoxy group refers for example to methoxy, trifluoromethoxy, ethoxy, n-propoxy, i-propoxy, n-butoxy, i-butoxy, s-butoxy, t-butoxy or 2-methylbutoxy.

The chemical unit D in the molecules of the invention has donor properties. The skilled person is aware in principle of what is meant by donor and acceptor properties, respectively. In one preferred embodiment the chemical unit D is electron-donating. It has a +M effect (positive mesomeric effect). In particular, suitable donor substituents have an atom with a free electron pair, such as an N, O or S atom, for example. Preferred in this context are 5-membered ring heteroaryl groups having precisely one ring heteroatom. These heteroaryl groups may also have further aryl groups fused to them. Especially preferred in that context are carbazole groups or carbazole derivates. Further suitable donor substituents are phenoxazine groups or phenoxazine derivatives. In the case of the latter, the oxygen of the phenoxazine may be replaced, for example, by —$CRR^1$, —C=$CRR^1$, —C=NR, —NR—, —$SiRR^1$—, —S—, —S(O)—, —S(O)$_2$—, O-interrupted substituted or unsubstituted C1-C9-alkylene, C2-C8-alkenylene, C2-C8-alkynylene or arylene group, phenyl units or substituted phenyl units. In one preferred embodiment the electron-withdrawing radical X exerts a –M effect (negative mesomeric effect) or a –I effect (negative inductive effect). The radical X, accordingly, is an acceptor substituent. Suitable acceptor substituents are, in particular, cyano groups or $CF_3$.

In ortho-position to the donor on the aromatic moiety, the molecules of the invention have a substituent. This permits effective separation of HOMO and LUMO of the organic molecule.

The molecules of the invention exhibit thermally activated delayed fluorescence and emit preferably in the dark blue region of the visible spectrum.

The use of the molecules of the invention in an optoelectronic device, such as an OLED, leads to higher efficiencies on the part of the device. Furthermore, OLEDs in the dark blue colour spectrum can be realized. Corresponding OLEDs have a greater stability than OLEDs with known emitter materials and of comparable colour.

The crosslinkable units QE comprise in one embodiment a compound selected from the group consisting of oxetanes, alkines and azides, more particularly for a click reaction, and also the following alkene derivatives:

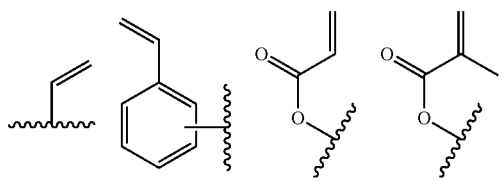

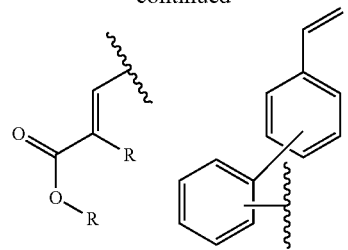

In an alternative embodiment, Z is a covalent single bond or a divalent organic bridge selected from substituted and unsubstituted alkylene (including branched or cyclic), alkenylene, alkynylene, arylene and heteroarylene groups, O, NR, C≡$CR_2$, C=NR, $SiR_2$ S, S(O), S(O)$_2$, BR, PR, P(O)R, with combinations of these units also being possible (for example O-interrupted alkylene (including branched or cyclic), alkenylene, alkynylene, arylene and heteroarylene groups).

In one preferred embodiment, D independently of one another is in each case a donor group having electron-donating properties, selected from the group consisting of substituted and unsubstituted carbazole, substituted or unsubstituted indole, substituted and unsubstituted indoline, substituted and unsubstituted dihydroacridine, substituted and unsubstituted benzimidazole, substituted and unsubstituted 2,3,4,9-tetrahydrocarbazole, substituted and unsubstituted 1,2,3,4-tetrahydroquinoline, substituted and unsubstituted phenothiazine, substituted and unsubstituted phenoxazine, substituted and unsubstituted dihydrophenazine, substituted and unsubstituted spiro compounds.

In one embodiment of the organic molecule, the donor group having electron-donating properties of the formula I-1 has a structure of the formula II:

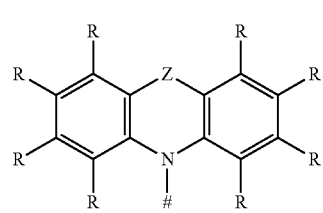

Formula II where the definitions of #, Z, and R are as stated above in connection with formula I.

The donor group having electron-donating properties of the formula I-1 may in one embodiment have a structure of the formula III:

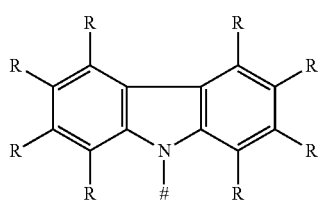

Formula III where the definitions of # and R are as stated above in connection with formula I.

Examples of donors of the invention:
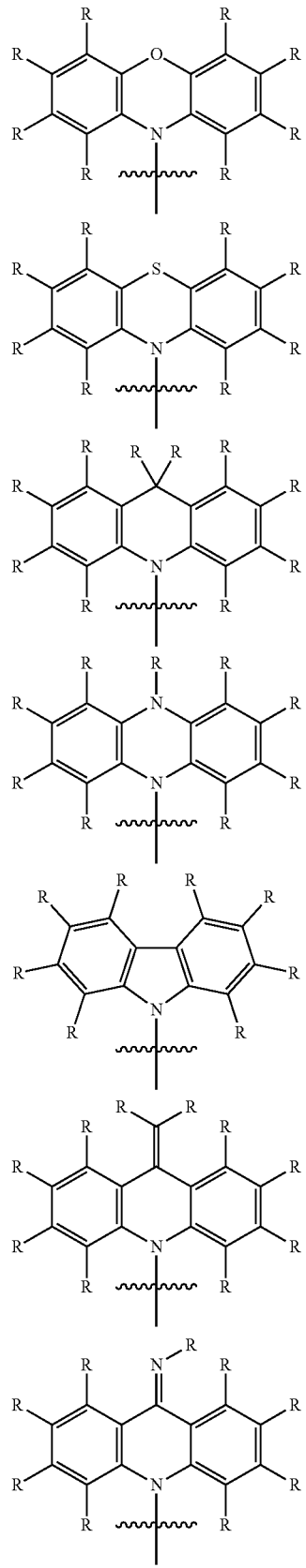
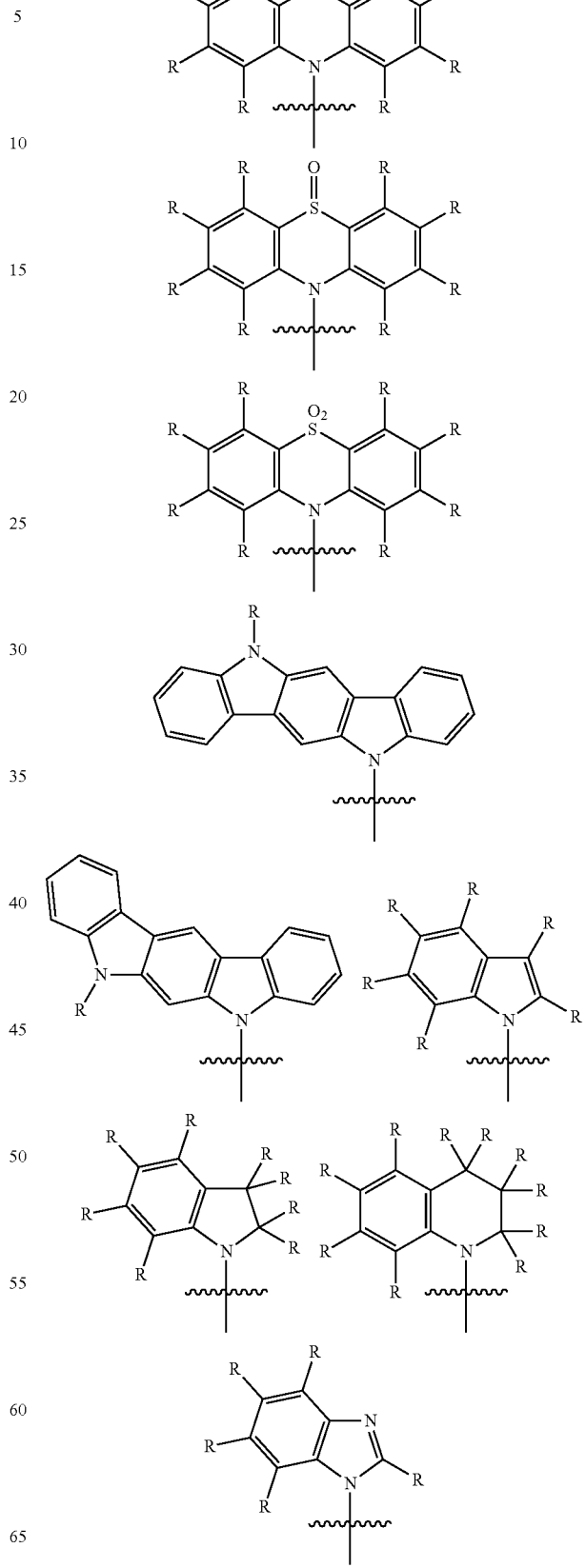

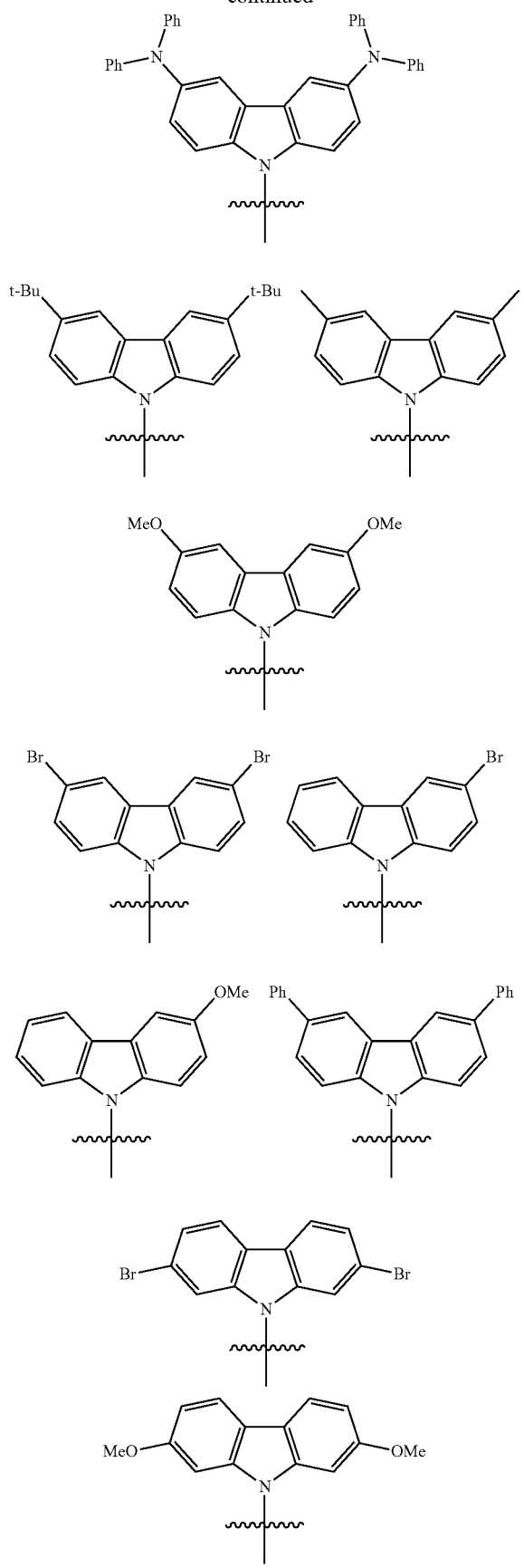

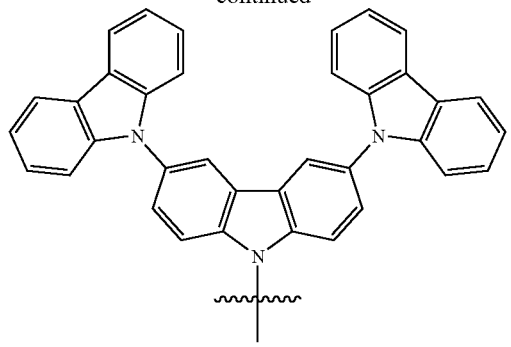

The accepting unit X of the formula I is CN in one embodiment and $CF_3$ in another embodiment. In a further embodiment of the invention, the radical R' of the formula I is a hydrogen atom, i.e. H.

The divalent group Y is an organic bridge which in one embodiment is a substituted or unsubstituted alkylene, alkenylene, alkynylene, arylene or heteroarylene group or a combination thereof, or is —O—, —NR—, —C=$CR_2$, —C=NR, —$SiR_2$— —S—, —S(O)—, —S(O)$_2$—, O-interrupted alkyl (including branched or cyclic), heteroalkyl, aryl, heteroaryl, alkenyl groups, phenyl units and substituted phenyl units; and the definitions of R are those stated above.

The bridge Y may be selected, for example, from one of the structures of the formulae IV to X:

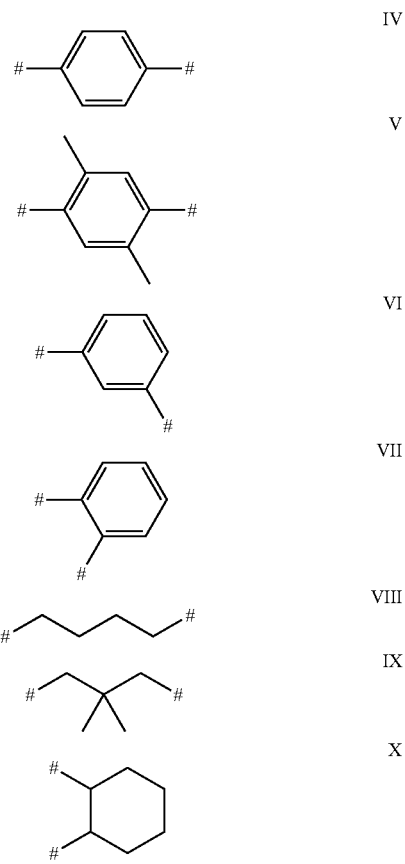

where
=attachment point of the bridge Y to the structure of formula I (i.e. to the positions of the first and second unit of the formula I, respectively, that are marked with R' and/or R").

In certain embodiments, the molecules of the invention have a structure of the formula XI-a, XI-b or XI-c:

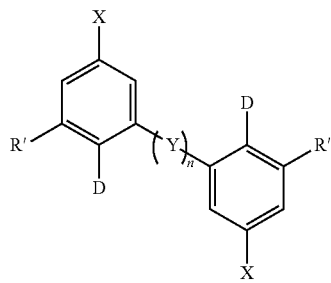

Formula XI-a

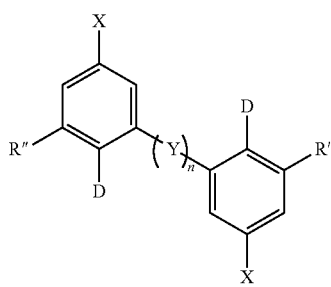

Formula XI-b

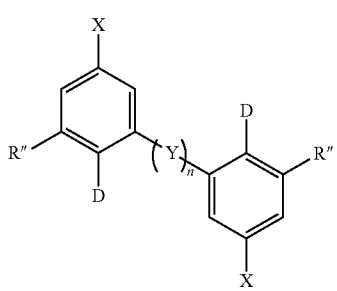

Formula XI-c where n=0 or 1;
and where the definitions of D, R', R", X and Y are those stated above.

In one embodiment the molecules of the invention have a structure of the formula XII.

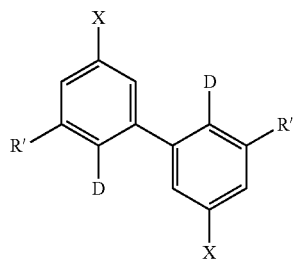

Formula XII and where the definitions of D, R' and X are those stated above.

In a further-preferred embodiment the molecules of the invention have a structure of the formula XIII:

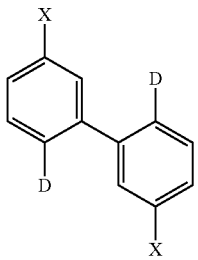

Formula XIII where the definitions of D and X are those stated above.

In a further aspect, the invention relates to a process for preparing an organic molecule of the invention, of the types described here.

The synthesis shown is that for the molecules of the invention having a single bond between the phenyl rings, and for a bond via a bridge Y, in each case with at least one optional subsequent reaction.

-continued

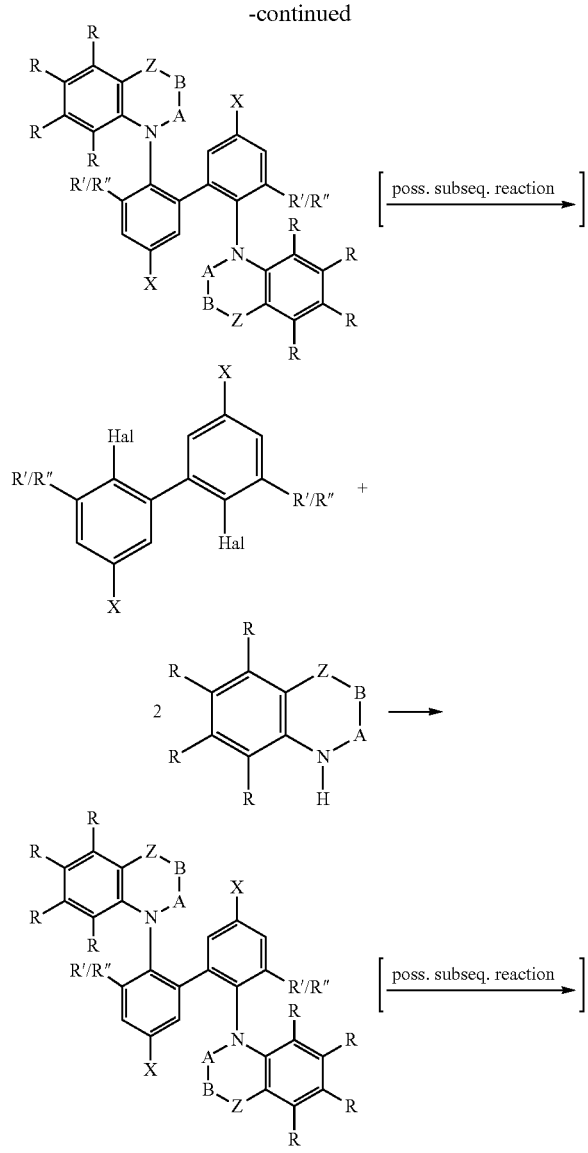

In this case a nitrogen heterocycle is reacted in a nucleophilic aromatic substitution with an aryl halide, preferably an aryl fluoride. Typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, preferably an aryl bromide, an aryl iodide, aryl triflate or an aryl tosylate.

The modes of preparation described may represent either the last synthetic reaction or else provide a precursor molecule which can be converted by subsequent reactions, as for example by altering the radicals R, R' and/or R", into the molecule of the invention.

A further aspect of the invention relates to the use of an organic molecule of the type described here as a luminescent emitter or as an absorber, and/or as host material and/or as electron transport material, and/or as hole injection material, and/or as hole blocking material in an organic optoelectronic device.

In the context of such use, the organic optoelectronic device is more particularly selected from the group consisting of:
   organic light-emitting diodes (OLEDs),
   light-emitting electrochemical cells,
   OLED sensors, especially in gas and vapour sensors not hermetically externally shielded,
   organic diodes,
   organic solar cells,
   organic transistors,
   organic field-effect transistors,
   organic lasers and
   down-conversion elements.

In the case of the use, the fraction of the organic molecule in the emission layer in an organic optoelectronic device, more particularly in OLEDs, is 1% to 99%, more particularly 5% to 80% (wt %). In an alternative embodiment, the proportion of the organic molecule in the emission layer is 100%.

In one embodiment, the light-emitting layer comprises not only the organic molecule of the invention but also a host material whose triplet (T1) and singlet (S1) energy levels are energetically higher than the triplet (T1) and singlet (S1) energy levels of the organic molecule.

In a further aspect, the invention relates to an organic optoelectronic device comprising an organic molecule of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

An organic optoelectronic device of this kind has in one embodiment:
   a substrate,
   an anode and
   a cathode, the anode or the cathode in particular being applied directly to the substrate, and
   at least one light-emitting layer which is disposed between anode and cathode and which comprises the organic molecule of the invention.

In one embodiment, the optoelectronic device is an OLED. A typical OLED has, for example, the following layer construction:
   1. Substrate (support material)
   2. Anode
   3. Hole injection layer (HIL)
   4. Hole transport layer (HTL)
   5. Electron blocking layer (EBL)
   6. Emitting layer (EML)
   7. Hole blocking layer (HBL)
   8. Electron transport layer (ETL)
   9. Electron injection layer (EIL)
   10. Cathode.

Certain layers are present only optionally. Moreover, a number of these layers may coincide with one another. And it is possible for certain layers to be present multiply in the component.

According to one embodiment, at least one electrode of the organic component is translucent in form. Here and below, "translucent" denotes a layer which is transmissive to visible light. This translucent layer may be transparently clear, i.e. transparent, or may be at least partly light-absorbing and/or partly light-scattering, so that the translucent layer may also, for example, have a diffuse or milky translucency. In particular, a layer identified here as translucent is as far as possible transparent in form, and so, in particular, the absorption of light is as small as possible.

According to a further embodiment, the organic component, more particularly an OLED, has an inverter construction. A feature of the inverter construction is that the cathode is located on the substrate and the other layers are applied, correspondingly, in inverted order:

1. Substrate (support material)
2. Cathode
3. Electron injection layer (EIL)
4. Electron transport layer (ETL)
5. Hole blocking layer (HBL)
6. Emitting layer (EML)
7. Electron blocking layer (EBL)
8. Hole transport layer (HTL)
9. Hole injection layer (HIL)
10. Anode Certain layers are present only optionally. Moreover, a number of these layers may coincide with one another. And it is possible for certain layers to be present multiply in the component.

In one embodiment, in the case of the inverted OLED, the anode layer of the typical construction, e.g. an ITO layer (indium tin oxide), is connected as cathode.

According to a further embodiment, the organic component, more particularly an OLED, has a stacked construction. In this case the individual OLEDs are arranged one above another and not, in the usual form, alongside one another. A stacked construction may permit the generation of mixed light. This construction may be used, for example, in the generation of white light, which is generated by imaging the entire visible spectrum typically through the combination of the emitted light from blue, green and red emitters. Furthermore, for virtually the same efficiency and identical luminance, significantly longer lifetimes can be achieved in comparison to conventional OLEDs. For the stacked construction, optionally, a layer known as a charge generation layer (CGL) is used between two OLEDs. This layer consists of an n-doped and a p-doped layer, the n-doped layer typically being applied closer to the anode.

In one embodiment—called a tandem OLED—there are two or more emission layers between anode and cathode. In one embodiment, three emission layers are arranged one above another, with one emission layer emitting red light, one emission layer emitting green light and one emission layer emitting blue light, and, optionally, further charge generation layers, blocking layers or transport layers are applied between the individual emission layers. In a further embodiment, the respective emission layers are applied directly adjacent. In another embodiment there is a charge generation layer between each of the emission layers. It is also possible for directly adjacent emission layers and emission layers separated by charge generation layers to be combined in an OLED.

Over the electrodes and the organic layers it is additionally possible for an encapsulating arrangement to be disposed. The encapsulating arrangement may be implemented for example in the form of a glass cover or in the form of a thin-film encapsulation.

Serving as support material for the optoelectronic device may be, for example, glass, quartz, plastic, metal, silicon wafer or any other suitable solid or flexible, optionally transparent material.

The support material may comprise, for example, one or more materials in the form of a layer, a film, a plate or a laminate.

Serving as anode in the optoelectronic device may be, for example, transparent conducting metal oxides such as, for example, ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$, or mixtures of different transparent conducting oxides.

Serving as materials of an HIL there may be, for example, PEDOT:PSS (poly-3,4-ethylenedioxythiophene:polystyrenesulfonic acid), PEDOT (poly-3,4-ethylenedioxy-thiophene), m-MTDATA (4,4',4"-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-[4-{N,N-bis(3-methyl-phenyl)amino}phenyl]-N-phenylamino]biphenyl), NPNPB (N,N'-diphenyl-N,N'-di-[4-(N,N-diphenylamino)phenyl]benzene), MeO-TPD (N,N,N',N'-tetrakis(4-methoxyphenyl)benzene), HAT-CN (1,4,5,8,9,11-hexaazatriphenylenehexa-carbonitrile) or Spiro-NPD (N,N'-diphenyl-N,N'-bis(1-naphthyl)-9,9'-spirobifluorene-2,7-diamine).

Serving as materials of an HTL may be tertiary amines, carbazole derivatives, polystyrenesulfonic acid-doped polyethylenedioxythiophene, camphorsulfonic acid-doped polyaniline, poly-TPD (poly(4-butylphenyldiphenylamine)), [alpha]-NPD (poly(4-butylphenyldiphenylamine)), TAPC (4,4'-cyclohexylidene-bis[N,N-bis(4-methylphenyl)-benzenamine]), TCTA (tris(4-carbazoyl-9-ylphenyl)amine), 2-TNATA (4,4',4"-tris[2-naphthyl(phenyl)amino]triphenylamine), Spiro-TAD, DNTPD, NPNPB, MeO-TPD, HAT-CN or TrisPcz (9,9'-diphenyl-6-(9-phenyl-9H-carbazol-3-yl)-9H,9'H-3,3'-bicarbazole).

The HTL may have a p-doped layer which comprises an inorganic or organic dopant in an organic hole-conducting matrix. Examples of inorganic dopants which an be utilized include transition metal oxides such as, for instance, vanadium oxide, molybdenum oxide or tungsten oxide. Organic dopants which can be used include, for example, tetrafluorotetracyanoquinodimethane (F4-TCNQ), copper pentafluorobenzoate (Cu(I)pFBz) or transition metal complexes.

Serving as materials of an electron blocking layer may be, for example, mCP (1,3-bis(carbazol-9-yl)benzene), TCTA, 2-TNATA, mCBP (3,3-di(9H-carbazol-9-yl)biphenyl), tris-Pcz (9,9'-diphenyl-6-(9-phenyl-9H-carbazol-3-yl)-9H,9'H-3,3'-bicarbazole), CzSi (9-(4-tert-butylphenyl)-3,6-bis(triphenylsilyl)-9H-carbazole), or DCB (N,N'-dicarbazolyl-1,4-dimethylbenzene).

The emitting layer EML comprises or consists of emitter material or a mixture comprising at least two emitter materials, and optionally of one or more host materials. Examples of suitable host materials are mCP, TCTA, 2-TNATA, mCBP, Sif87 (dibenzo[b,d]thiophen-2-yltriphenylsilane), Sif88 (dibenzo[b,d]thiophen-2-yl)diphenylsilane), CBP (4,4'-bis-(N-carbazolyl)biphenyl) or DPEPO (bis[2-((oxo)diphenylphosphino)phenyl] ether). For emitter material emitting in the green or in the red, or a mixture comprising at least two emitter materials, the common matrix materials such as CBP are suitable. For emitter material emitting in the blue or a mixture comprising at least two emitter materials, it is possible to use UHG matrix materials (Ultra-High energy Gap materials) (see, for example, M. E. Thompson et al., Chem. Mater. 2004, 16, 4743) or other so-called Wide-Gap matrix materials.

The hole blocking layer HBL may comprise, for example, BCP (2,9-dimethyl-4,7-diphenyl-1,10-phenanthroline= bathocuproin), bis(2-methyl-8-hydroxyquinolinato)-(4-phenylphenolato)-aluminium(III) (BAlq), Nbphen (2,9-bis(naphthalen-2-yl)-4,7-diphenyl-1,10-phenanthroline), Alq3 (aluminium-tris(8-hydroxyquinolin)), TSPO1 (diphenyl-4- triphenylsilylphenylphosphine oxide) or TCB/TCP (1,3,5-tris(N-carbazolyl)benzene/1,3,5-tris(carbazol-9-yl)benzene).

The electron transport layer ETL may comprise, for example, materials based on AlQ$_3$, TSPO1, BPyTP2 (2,7-di(2,2'-bipyridin-5-yl)triphenyl) or BTB (4,4'-bis[2-(4,6-diphenyl-1,3,5-triazinyl)]-1,1'-biphenyl).

Examples of materials which can be used in a thin electron injection layer EIL include CsF, LiF, 8-hydroxyquinolinolatolithium (Liq), Li$_2$O, BaF$_2$, MgO or NaF.

Serving as materials of the cathode layer may be metals or alloys, for example Al, Al>AlF, Ag, Pt, Au, Mg, Ag:Mg. Typical layer thicknesses are 100-200 nm. Particular preference is given to using one or more metals which are stable in air and/or which are self-passivating, by formation of a thin protective oxide layer, for example.

Examples of materials suitable for encapsulation are aluminium oxide, vanadium oxide, zinc oxide, zirconium oxide, titanium oxide, hafnium oxide, lanthanum oxide and tantalum oxide. The skilled person here is aware of which combinations of the materials to use for an optoelectronic device comprising an organic molecule of the invention.

In one embodiment of the organic optoelectronic device of the invention, the organic molecule of the invention is used as emission material in a light-emitting layer, being used either as a pure layer or in combination with a matrix material.

The fraction of the organic molecule of the invention in the emission layer in a further embodiment, in a light-emitting layer in optical light-emitting devices, more particularly in OLEDs, is between 5% and 80%. In one embodiment of the organic optoelectronic device of the invention, the light-emitting layer is applied to a substrate; preferably an anode and a cathode are applied to the substrate and the light-emitting layer is applied between anode and cathode.

The light-emitting layer may exclusively have an organic molecule of the invention at 100% concentration, with the anode and the cathode applied to the substrate, and the light-emitting layer applied between anode and cathode.

In one embodiment of the organic optoelectronic device of the invention, a hole and electron injecting layer is applied between anode and cathode, and a hole and electron transporting layer is applied between hole and electron injecting layer, and the light-emitting layer is applied between hole and electron transporting layer.

In a further embodiment of the invention, the organic optoelectronic device comprises the following: a substrate, an anode, a cathode, and in each case at least one hole and electron injecting layer, and in each case at least one hole and electron transporting layer, and at least one light-emitting layer, comprising organic molecule of the invention and a host material whose triplet (T1) and singlet (S1) energy levels are energetically higher than the triplet (T1) and singlet (S1) energy levels of the organic molecule, with the anode and the cathode being applied to the substrate, and the hole and electron injecting layer being applied between anode and cathode, and the hole and electron transporting layer being applied between hole and electron injecting layer, and the light-emitting layer being applied between hole and electron transporting layer.

Also in accordance with the invention is a light-emitting material comprising an organic molecule of the invention and a host material, the triplet (T1) and singlet (S1) energy levels of the host material being energetically higher than the triplet (T1) and singlet (S1) energy levels of the organic molecule, where the light-emitting material emits fluorescence or thermally activated delayed fluorescence, and has a deltaE(S1–T1) value between the lowermost excited singlet (S1) state and the triplet (T1) state beneath it of less than 3000 cm$^{-1}$.

In a further aspect, the invention relates to a method for producing an optoelectronic component. In this case an organic molecule of the invention is used.

In one embodiment, the production method comprises the processing of the organic molecule of the invention by means of a vacuum evaporation process or from a solution.

Also in accordance with the invention is a method for producing an optoelectronic device of the invention that comprises at least one layer of the optoelectronic device
 being coated by a sublimation process,
 being coated by an OVPD (Organic Vapour Phase Deposition) process,
 being coated by carrier gas sublimation, and/or
 being produced from solution or by a printing process.

EXAMPLES

General Operating Protocols: Photophysical Measurements

Pretreatment of Optical Glasses

After each use, the optical glasses (cuvettes and substrates made of fused silica, diameter: 1 cm) are cleaned. Washed three times each with dichloromethane, acetone, ethanol, demineralized water. Placed in 5% Hellmanex solution for 24 h, rinsed off thoroughly with demineralized water, blown with nitrogen to dry the optical glasses.

Sample Preparation: Solutions 1-2 mg of the sample were dissolved in 100 ml of the respective solvent, concentration $10^{-5}$ mol/l. The cuvette was given an airtight closure and degassed for 10 minutes.

Sample Preparation, Film: Spin Coating

Instrument: Spin150, SPS euro.

The sample concentration was 10 mg/ml, prepared in toluene or chlorobenzene.

Program: 1) 3 s at 400 rpm; 2) 20 sec. at 1000 rpm at 1000 rpm/s; 3) 10 s at 4000 rpm at 1000 rpm/s. After coating, the films were dried in air at 70° C. for 1 minute on a precision hotplate from LHG.

Absorption Spectroscopy

Solutions:

UV-VIS spectra were recorded on an Evolution 201 instrument from Thermo Scientific. (See sample preparation: solutions)

Photoluminescence Spectroscopy and TCSPC

Steady-state emission spectroscopy is carried out using a FluoroMax-4 fluorescence spectrometer from Horiba Scientific, equipped with a 150 W xenon arc lamp, excitation and emission monochromators and a Hamamatsu R928 photomultiplier tube, and also with a TCSPC option. Emission and excitation spectra were corrected using standard correction plots.

Determination of Quantum Efficiency

The photoluminescent quantum yield was measured using an Absolute PL Quantum Yield Measurement C9920-03G system from Hamamatsu Photonics. This system consists of a 150 W xenon gas discharge lamp, automatically adjustable Czerny-Turner monochromators (250-950 nm) and an Ulbricht sphere with highly reflective Spektralon (a Teflon derivative) coating, connected via a glass fibre cable to a PMA-12 multichannel detector with BT (back thinned) CCD chip with 1024×122 pixels (size 24×24 μm). The quantum efficiency and the CIE coordinates were analyzed using the U6039-05 software, version 3.6.0.

The emission maximum is reported in nm, the quantum yield Φ in % and the CIE colour coordinates as x,y values.

PLQY was determined for polymer films, solutions and powder samples in accordance with the following protocol:

The reference material used is anthracene in ethanol at known concentration. First the absorption maximum of the sample was determined, and used to excite the sample.

Subsequently the absolute quantum yield was determined on degassed solutions and films under a nitrogen atmosphere.

The calculation was made by the system itself in accordance with the following equation:

$$\Phi_{PL} = \frac{n_{photon}, \text{emitted}}{n_{photon}, \text{absorbed}} = \frac{\int \frac{\lambda}{hc} \left[ Int_{emitted}^{Sample}(\lambda) - Int_{absorbed}^{Sample}(\lambda) \right] d\lambda}{\int \frac{\lambda}{hc} \left[ Int_{emitted}^{Reference}(\lambda) - Int_{absorbed}^{Reference}(\lambda) \right] d\lambda}$$

with the photon number $n_{photon}$ and the intensity Int.

Calculations According to Density Functional Theory

Molecular structures were optimized using the BP86 functional (Becke, A. D. Phys. Rev. A1988, 38, 3098-3100; Perdew, J. P. Phys. Rev. B 1986, 33, 8822-8827), employing the resolution-of-identity (RI) approximation (Sierka, M.; Hogekamp, A.; Ahlrichs, R. J. Chem. Phys. 2003, 118, 9136-9148; Becke, A. D., J. Chem. Phys. 98 (1993) 5648-5652; Lee, C; Yang, W; Parr, R. G. Phys. Rev. B 37 (1988) 785-789). Excitation energies were calculated in the case of the structure optimized with BP86 by the time-dependent DFT (TD-DFT) method using the B3LYP functional (Becke, A. D., J. Chem. Phys. 98 (1993) 5648-5652; Lee, C; Yang, W; Parr, R. G. Phys. Rev. B 37 (1988) 785-789; Vosko, S. H.; Wilk, L.; Nusair, M. Can. J. Phys. 58 (1980) 1200-1211; Stephens, P. J.; Devlin, F. J.; Chabalowski, C. F.; Frisch, M. J. J. Phys. Chem. 98 (1994) 11623-11627). All calculations use def2-SV(P) base sets (Weigend, F.; Ahlrichs, R. Phys. Chem. Chem. Phys. 2005, 7, 3297-3305; Rappoport, D.; Furche, F. J. Chem. Phys. 2010, 133, 134105/1-134105/11) and an m4 grid for numeric integration. All DFT calculations were carried out using the Turbomole program package (Version 6.5) (TURBOMOLE V6.4 2012, a development by Karlsruhe University and Forschungszentrum Karlsruhe GmbH, 1989-2007, TURBOMOLE GmbH, since 2007; http://www.turbomole.com).

Example 1

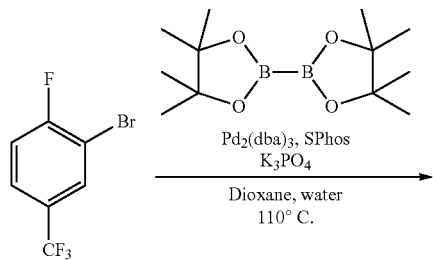

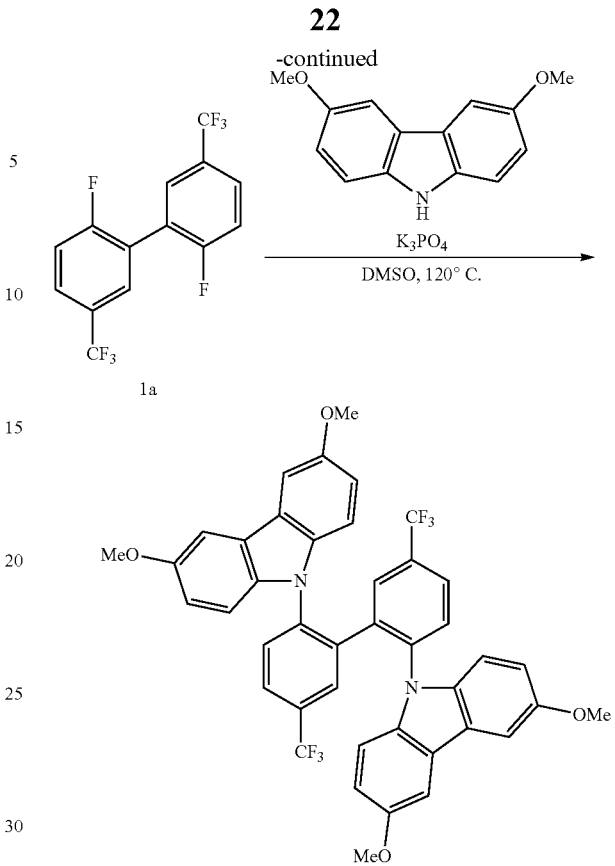

Stage 1:

3-Bromo-4-fluorobenzotrifluoride (65.8 mmol), bis(pinacolato)diboron (32.9 mmol), Pd$_2$(dba)$_3$ (0.33 mmol), SPhos (1.32 mmol) and tribasic potassium phosphate (197 mmol) are stirred under nitrogen in a dioxane/water mixture (300 ml/20 ml) of 110° C. for 16 hours. The insoluble constituents of the reaction mixture are subsequently removed by filtration, the material on the filter being washed with dioxane. The solvent of the filtrate is removed and the residue obtained is dissolved in dichloromethane and filtered through a little silica gel. The product is obtained as a yellow solid. $^1$H NMR (500 MHz, chloroform-d) δ=7.72-7.69 (m, 4H), 7.34-7.31 (m, 2H) ppm.

Stage 2:

1a (5 mmol), 3,6-dimethoxycarbazole (12 mmol) and tribasic potassium phosphate (20 mmol) are suspended under nitrogen in DMSO (20 ml) and stirred at 100° C. (16 hours). The reaction mixture is then introduced into 150 ml of water and extracted with dichloromethane (2×100 ml). The combined organic phases are washed with saturated sodium chloride solution (2×150 ml) and dried over magnesium sulfate and then the solvent is removed. The crude product was taken up in dichloromethane and filtered through a little silica gel (eluent: dichloromethane). Lastly, following removal of the solvent, purification took place by recrystallization from a mixture of ethanol and chloroform. The product 1 was obtained as a white solid.

$^1$H NMR (500 MHz, chloroform-d) δ 8.15 (d, J=2.1 Hz, 2H), 7.59 (dd, J=8.3, 2.1 Hz, 2H), 7.23 (d, J=8.3 Hz, 3H), 6.94 (br s, 2H), 6.79-6.48 (br m, 4H), 6.36 (br s, 2H), 5.68 (br s, 2H), 3.86 (s, 12H).

The film emission of 1 (10% in PMMA) can be seen in FIG. 1. The emission maximum is at 461 nm. The photoluminescence quantum yield (PLQY) is 47%.

Example 2

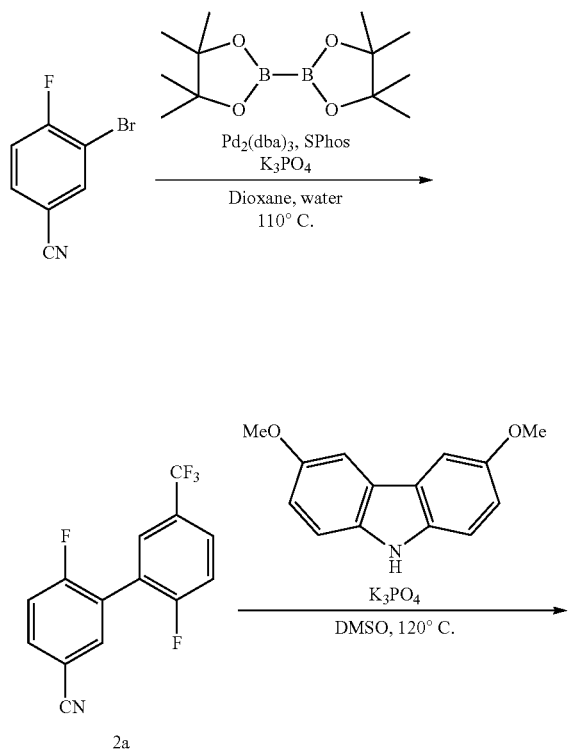

Stage 1:

3-Bromo-4-fluorobenzonitrile (125 mmol), bis(pinacolato)diboron (62.5 mmol), Pd$_2$(dba)$_3$ (0.63 mmol), SPhos (2.50 mmol) and tribasic potassium phosphate (375 mmol) are stirred under nitrogen in a dioxane/water mixture (350 ml/20 ml) at 110° C. for 16 hours. The insoluble constituents of the reaction mixture are subsequently removed by filtration, the material on the filter being washed with dioxane. The solvent of the filtrate is removed and the residue obtained is dissolved in tetrahydrofuran and filtered through a little silica gel. The product is obtained as a yellow solid. $^1$H NMR (500 MHz, chloroform-d) b=7.79-7.76 (m, 2H), 7.74-7.73 (m, 2H), 7.36-7.33 (m, 2H) ppm.

Stage 2:

2a (8.33 mmol), 3,6-dimethoxycarbazole (19.2 mmol) and tribasic potassium phosphate (33.3 mmol) are suspended under nitrogen in DMSO (30 ml) and stirred at 110° C. (16 hours). The reaction mixture is then introduced into 400 ml of saturated sodium chloride solution and extracted with dichloromethane (3×150 ml). The combined organic phases are washed with saturated sodium chloride solution (2×150 ml) and dried over magnesium sulfate and then the solvent is removed. The crude product, finally, was purified by recrystallization from toluene The product 2 was obtained as a yellow solid.

$^1$H NMR (500 MHz, chloroform-d) b=8.19 (d, J=1.9 Hz, 2H), 7.62 (dd, J=8.3, 2.0 Hz, 2H), 7.24 (d, J=8.3 Hz, 2H), 7.21 (br s, 2H), 6.87 (br s, 2H), 6.72 (br s, 2H), 6.49 (br s, 2H), 6.38 (br s, 2H), 5.65 (br s, 2H), 3.94-3.75 (m, 12H).

Figure 2:
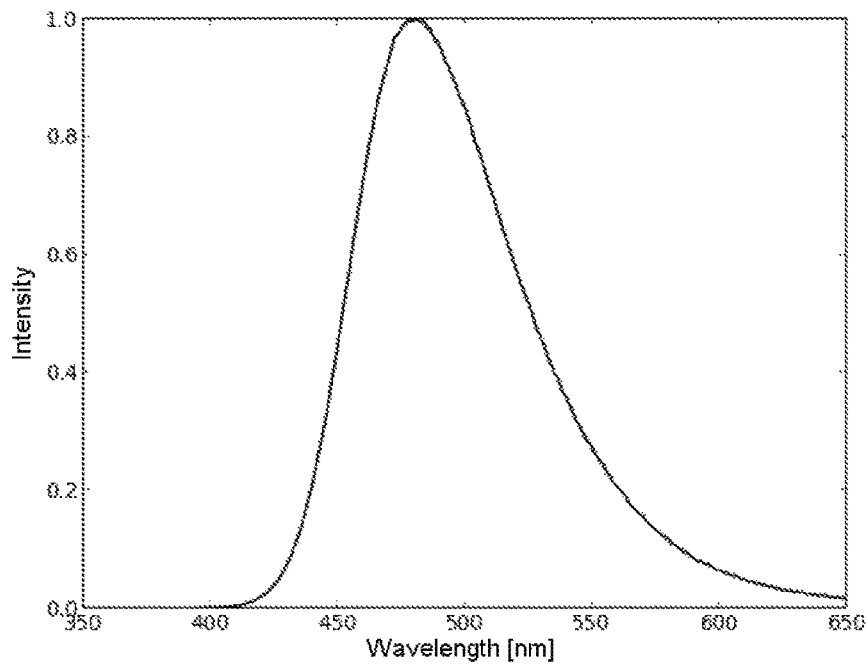
FIG. 2 is a film emission of product 2 (10% in PMMA).

The film emission of 2 (10% in PMMA) can be seen in FIG. 2. The emission maximum is at 478 nm. The photoluminescence quantum yield (PLQY) is 75%. The emission lifetime is 25 μs.

Example 3

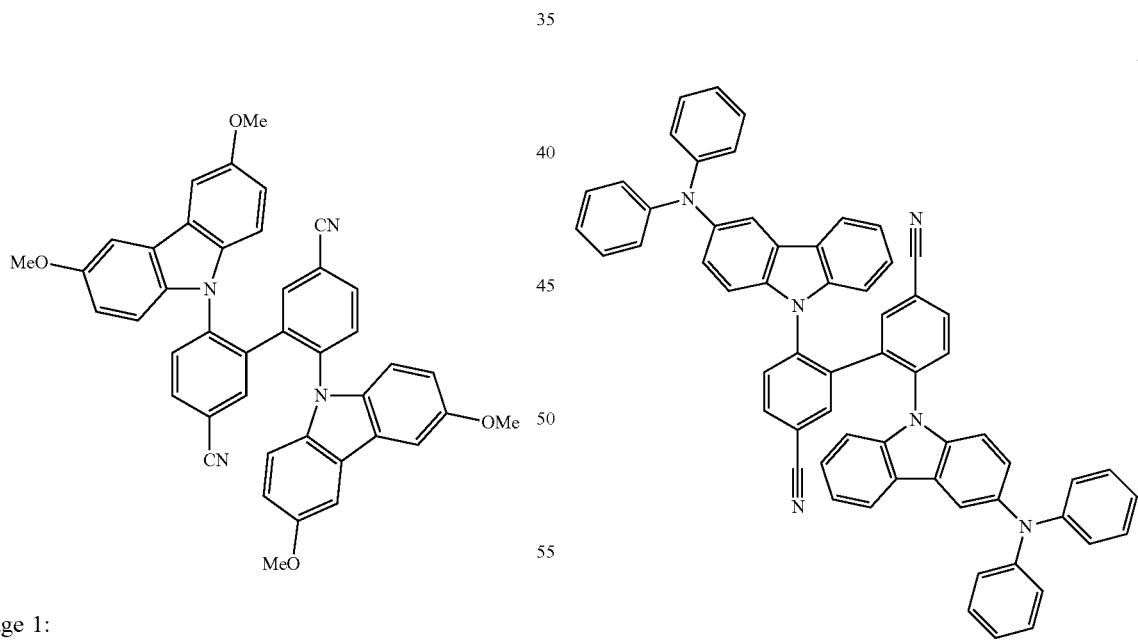

Thin-layer chromatography: R$_f$=0.5 (cyclohexane/ethyl acetate 5:1)

Figure 3:
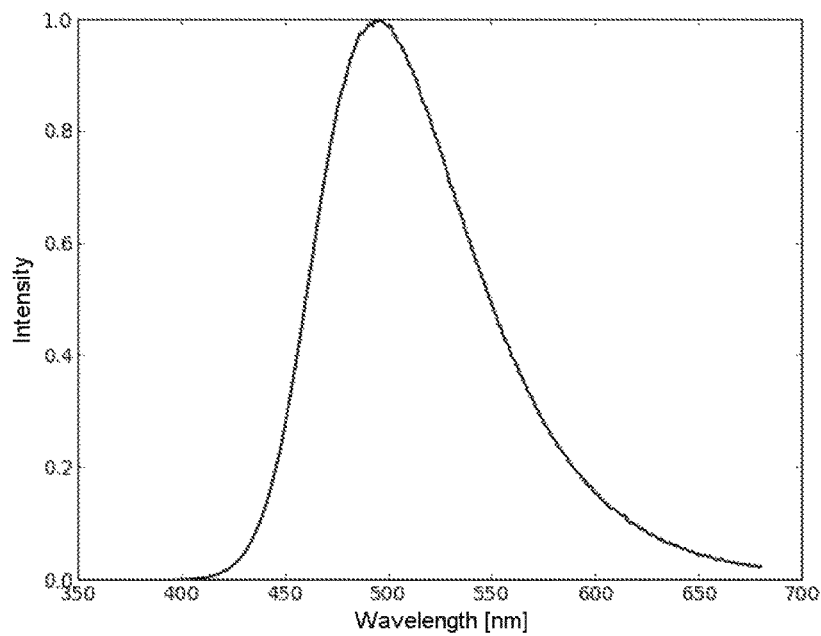
FIG. 3 is a film emission of product 3 (10% in PMMA).

The film emission of 3 (10% in PMMA) can be seen in FIG. 3. The emission maximum is at 495 nm. The photoluminescence quantum yield (PLQY) is 64%. The emission lifetime is 13 μs.

Example 4

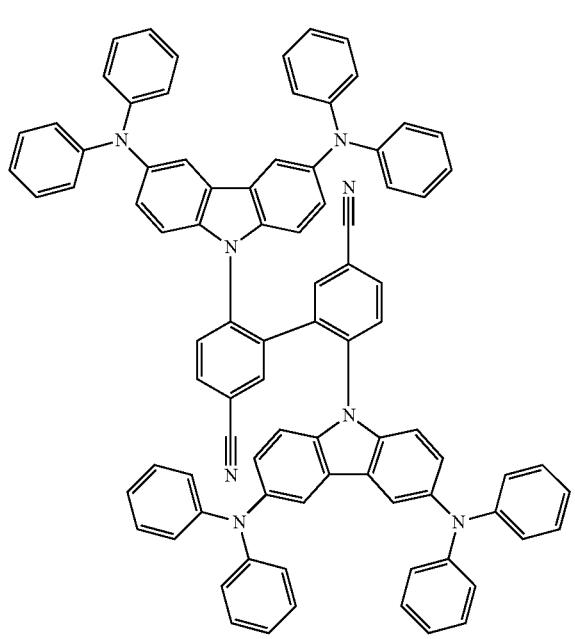

4

Thin-layer chromatography: $R_f$=0.5 (cyclohexane/ethyl acetate 5:1)

Figure 4:
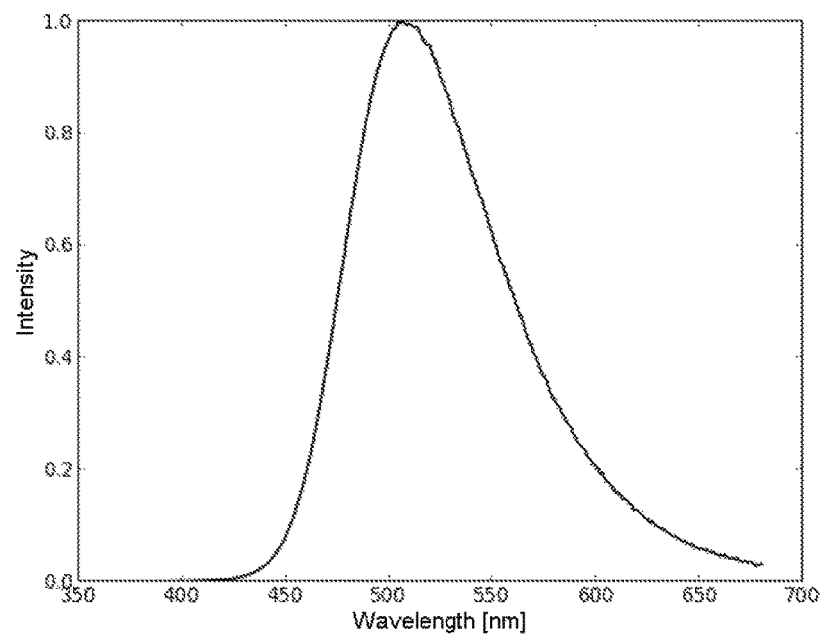
FIG. 4 is a film emission of product 4 (10% in PMMA).

The film emission of 4 (10% in PMMA) can be seen in FIG. 4. The emission maximum is at 507 nm. The photoluminescence quantum yield (PLQY) is 66%. The emission lifetime is 10 μs.

Example 5

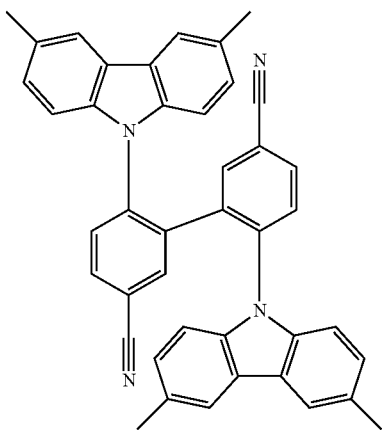

5

Thin-layer chromatography: $R_f$=0.5 (cyclohexane/ethyl acetate 5:1)

Figure 5:
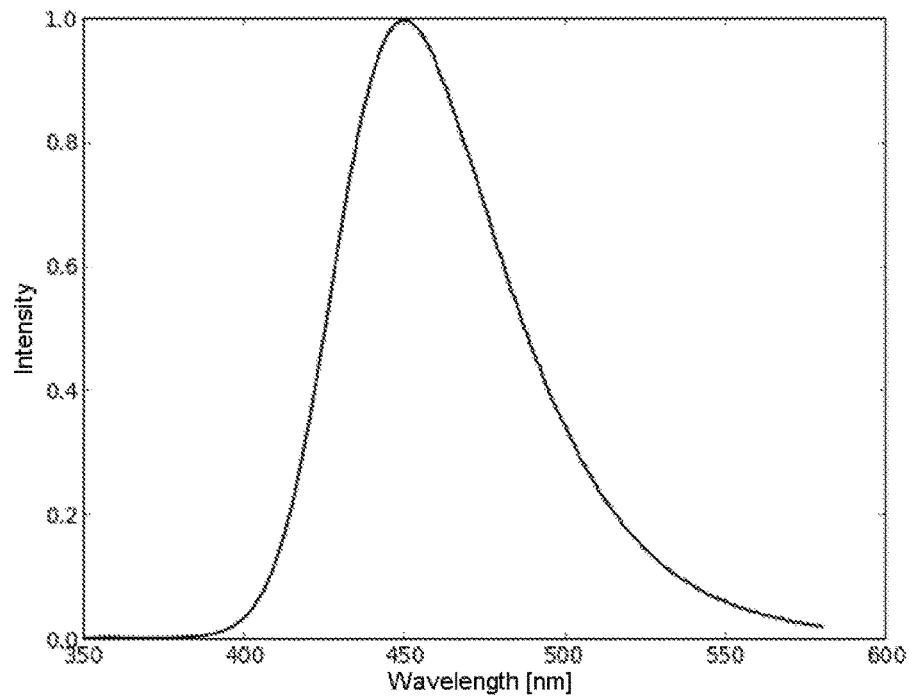
FIG. 5 is a film emission of product 5 (10% in PMMA).

The film emission of 5 (10% in PMMA) can be seen in FIG. 5. The emission maximum is at 450 nm. The photoluminescence quantum yield (PLQY) is 62% and the full width at half maximum (FWHM) is 64 nm.

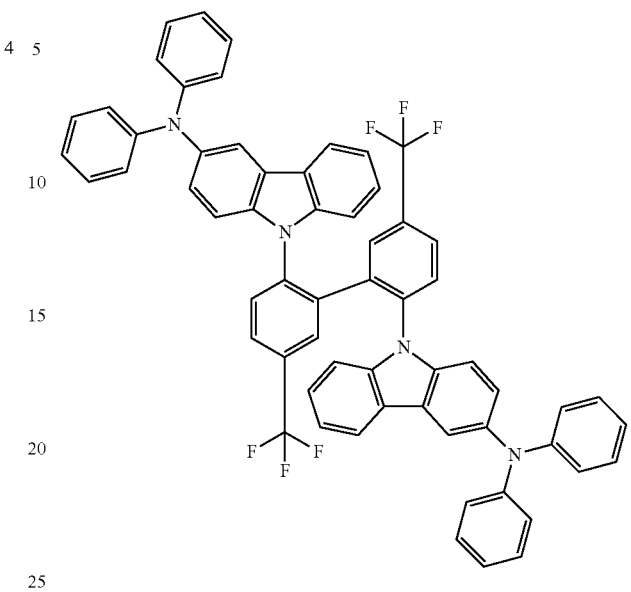

6

Thin-layer chromatography: $R_f$=0.6 (cyclohexane/ethyl acetate 10:1)

Figure 6:
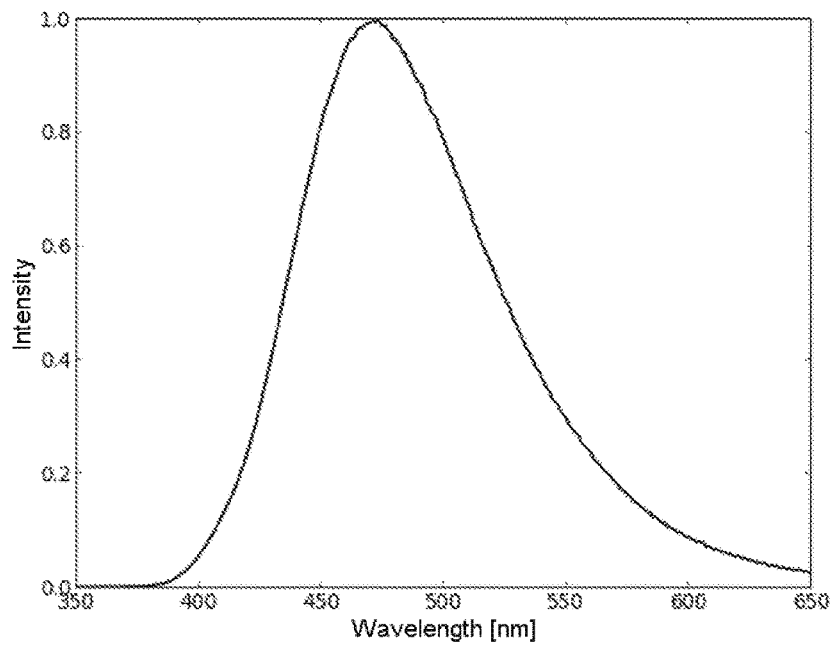
FIG. 6 is a film emission of product 6 (10% in PMMA).

The film emission of 6 (10% in PMMA) can be seen in FIG. 6. The emission maximum is at 472 nm. The photoluminescence quantum yield (PLQY) is 32%.

Example 7

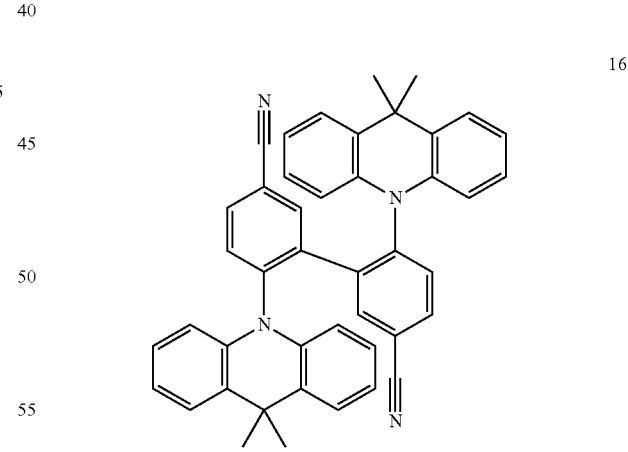

16

$^1$H NMR (500 MHz, chloroform-d) δ 7.79 (dd, J=8.2, 2.0 Hz, 2H), 7.63 (d, J=2.0 Hz, 2H), 7.48-7.32 (m, 6H), 7.20-5.30 (br m, J=510.3 Hz, 12H), 1.87 (s, 6H), 0.80 (s, 6H).

Figure 7:
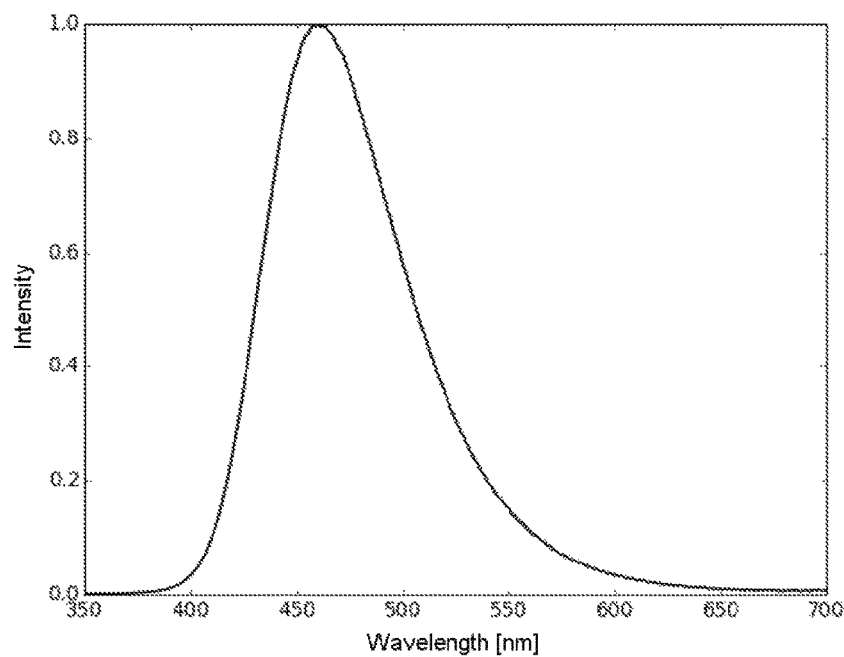
FIG. 7 is a film emission of product 7 (10% in PMMA).

The film emission of 7 (10% in PMMA) can be seen in FIG. 7. The emission maximum is at 471 nm. The photoluminescence quantum yield (PLQY) is 65% and the full width at half maximum (FWHM) is 83 nm. The emission lifetime is 21 μs.

Example 8

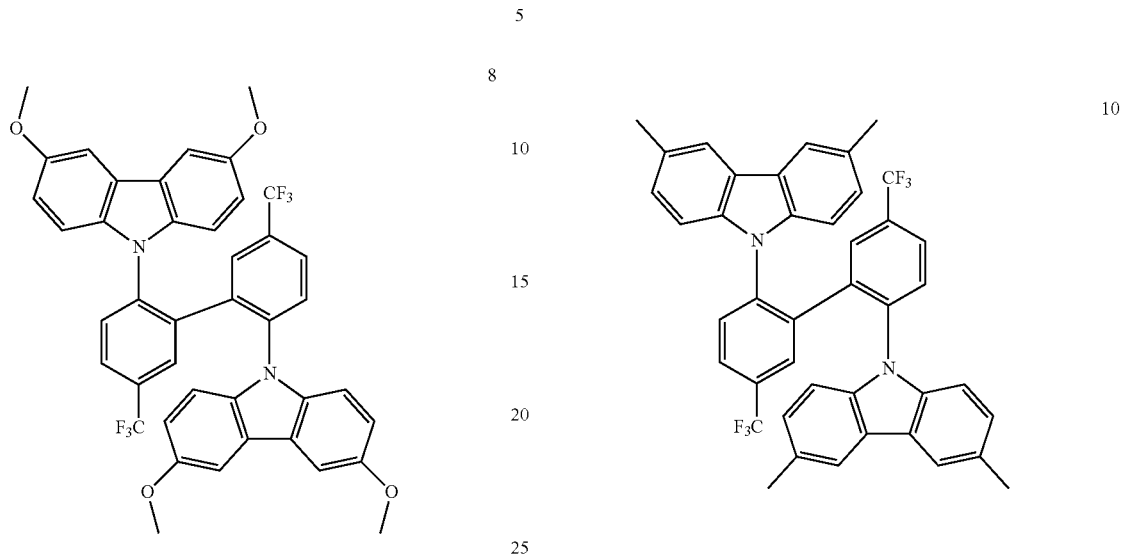

The film emission of 8 (10% in PMMA) was measured. The emission maximum is at 461 nm.

The photoluminescence quantum yield (PLQY) is 47%. The full width at half maximum (FWHM) is 76 nm.

Example 9

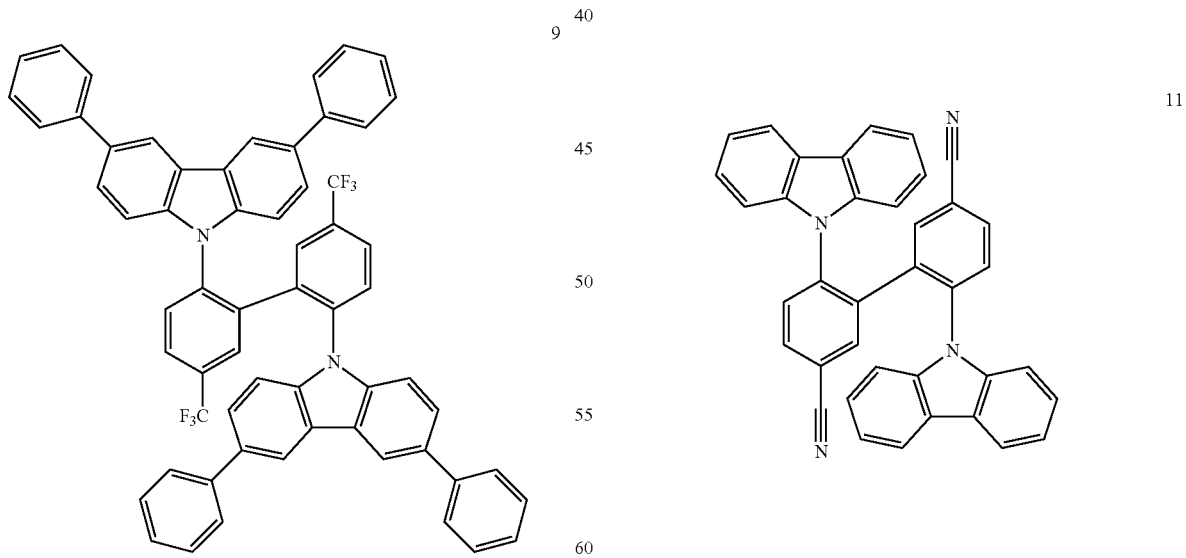

Figure 9:
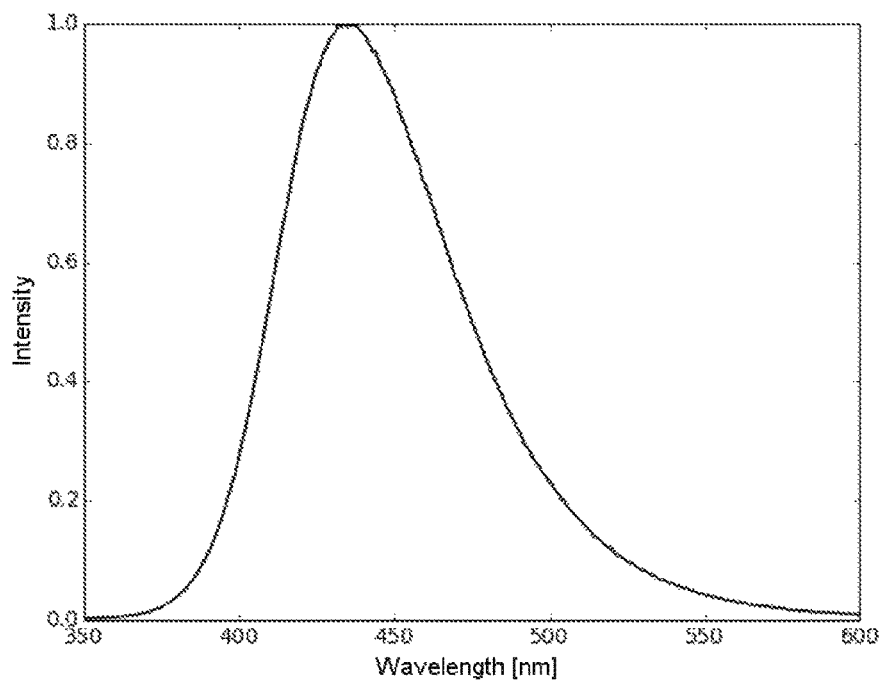
FIG. 9 is a film emission of product 9 (10% in PMMA).

The film emission of 9 (10% in PMMA) can be seen in FIG. 9. The emission maximum is at 430 nm. The photoluminescence quantum yield (PLQY) is 23%. The full width at half maximum (FWHM) is 76 nm.

Example 10

Figure 10:
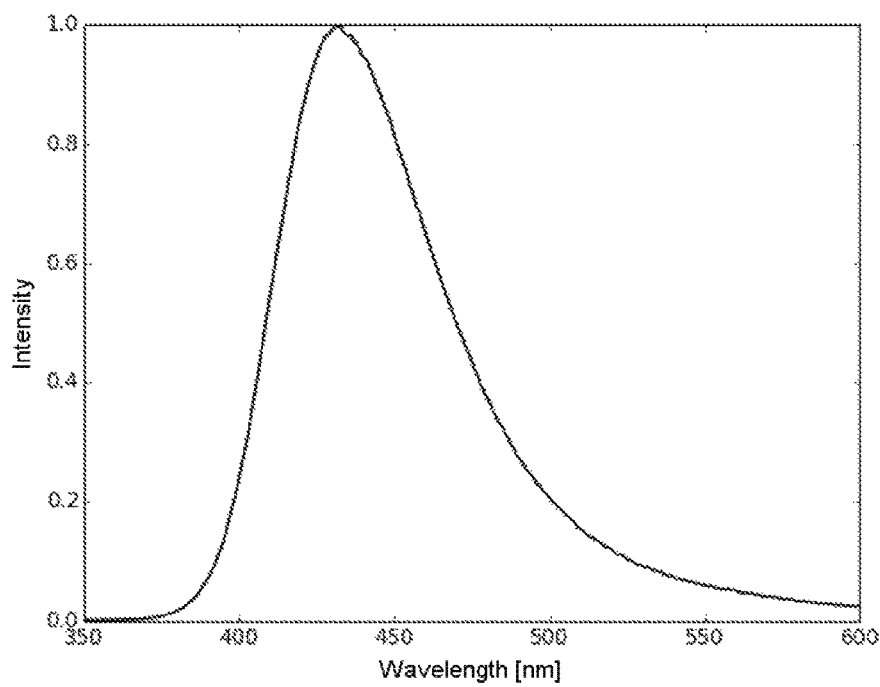
FIG. 10 is a film emission of product 10 (10% in PMMA).

The film emission of 10 (10% in PMMA) can be seen in FIG. 10. The emission maximum is at 434 nm. The photoluminescence quantum yield (PLQY) is 30%. The full width at half maximum (FWHM) is 67 nm.

Example 11

Figure 11:
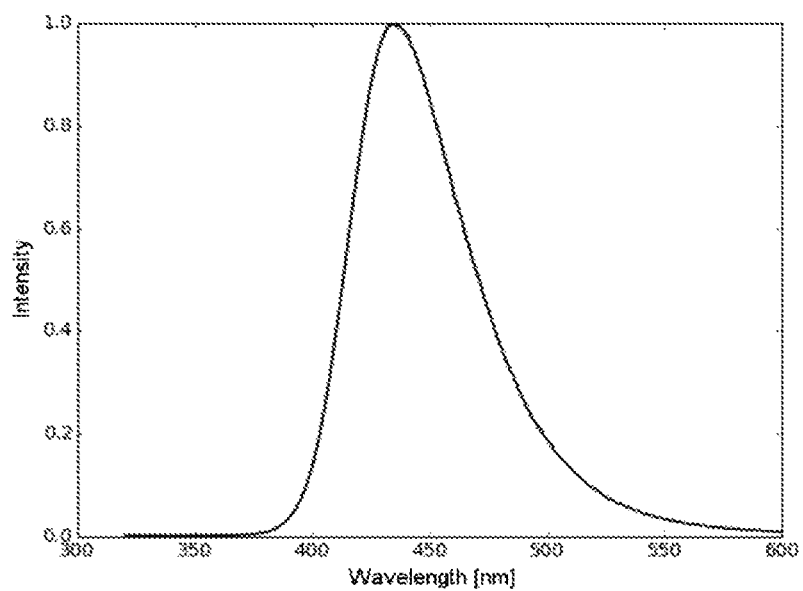
FIG. 11 is a film emission of product 11 (10% in PMMA).
Figure 12:
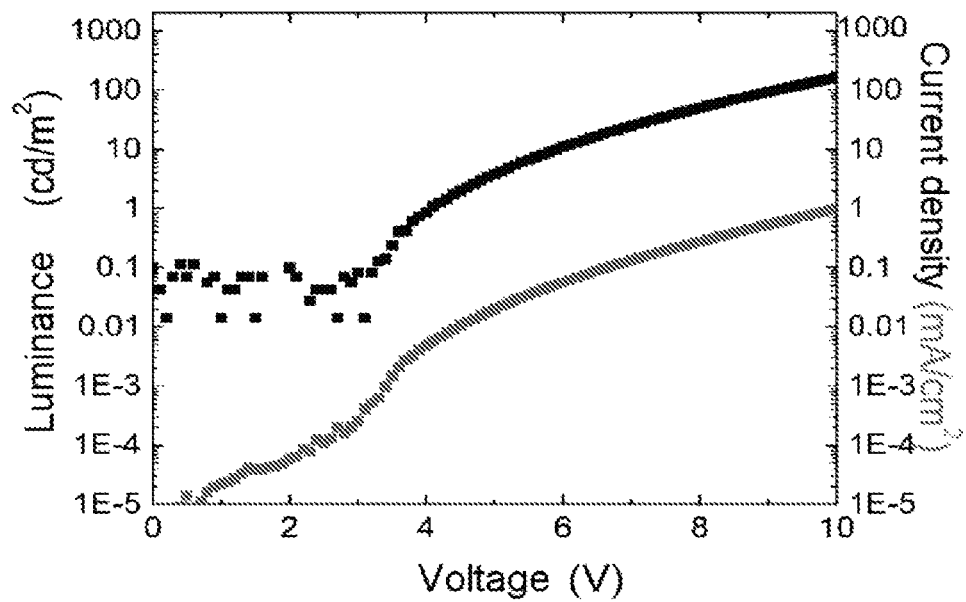
FIG. 12 is the current density and luminance of OLED component X3.
Figure 13:
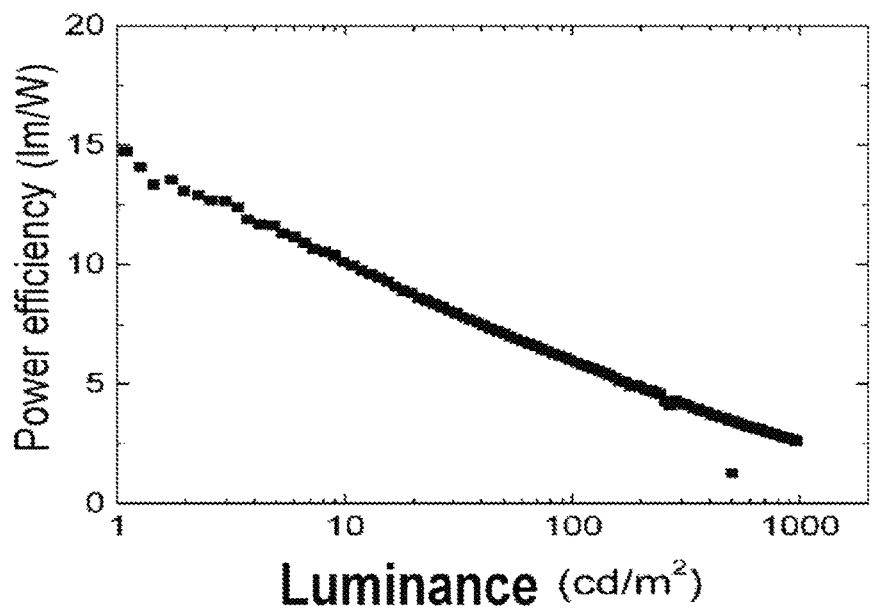
FIG. 13 is the power efficiency of OLED component X3.
Figure 14:
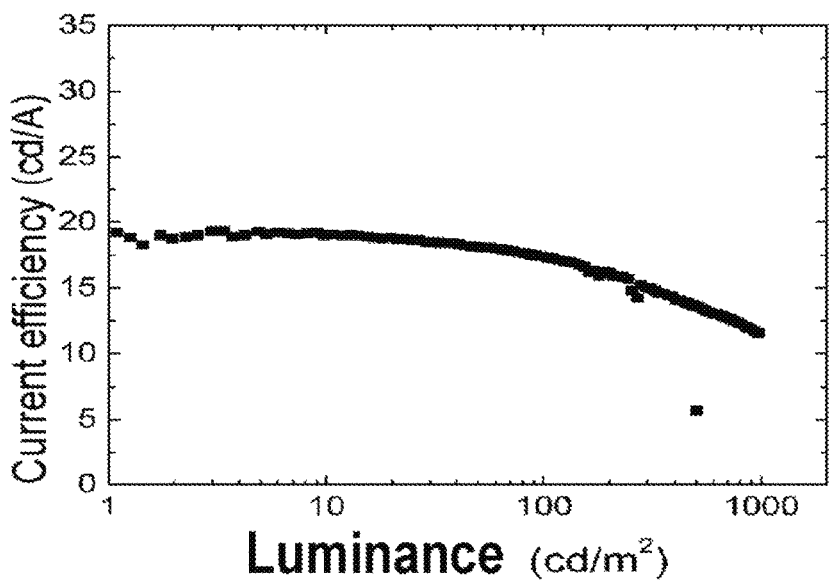
FIG. 14 is the current efficiency of OLED component X3.
Figure 15:
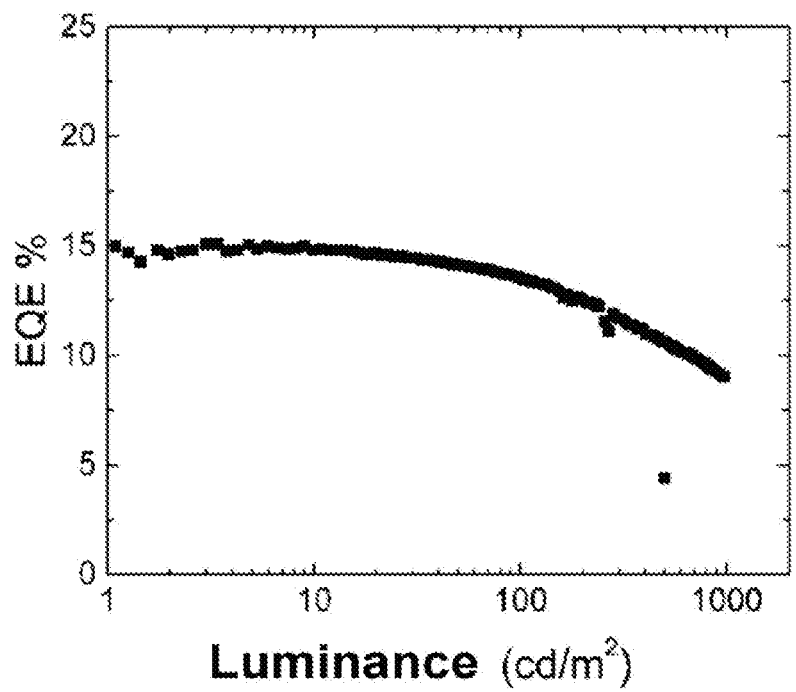
FIG. 15 is the external quantum efficiency of OLED component X3.
Figure 16:
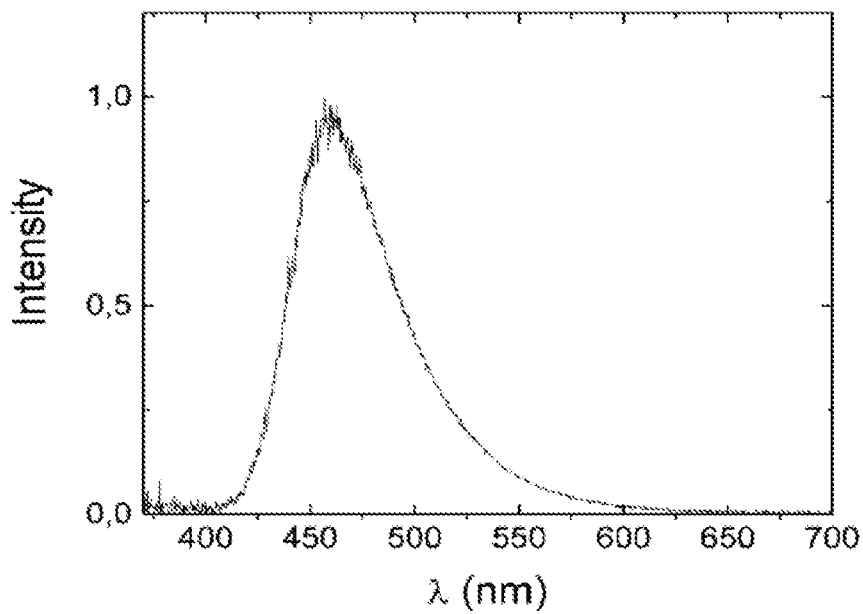
FIG. 16 is the electroluminescence spectrum of OLED component X3, operated at 14 V.

The film emission of 11 (10% in PMMA) can be seen in FIG. 11. The emission maximum is at 432 nm. The photoluminescence quantum yield (PLQY) is 42%. The full width at half maximum (FWHM) is 62 nm.

Example 12

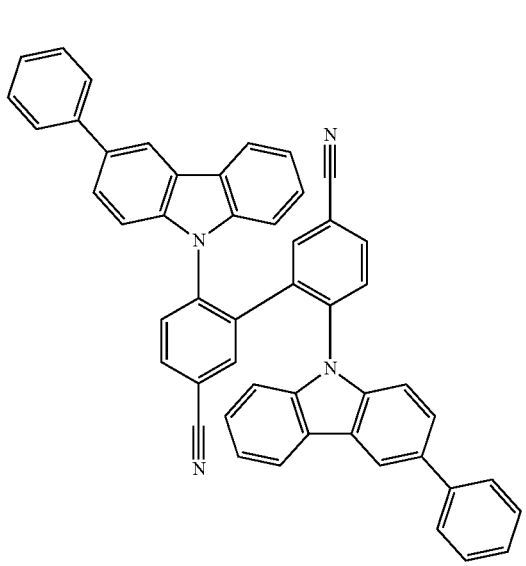

12

The film emission of 12 (10% in PMMA) was measured. The emission maximum is at 441 nm. The photoluminescence quantum yield (PLQY) is 58%. The full width at half maximum (FWHM) is 61 nm.

Example 13

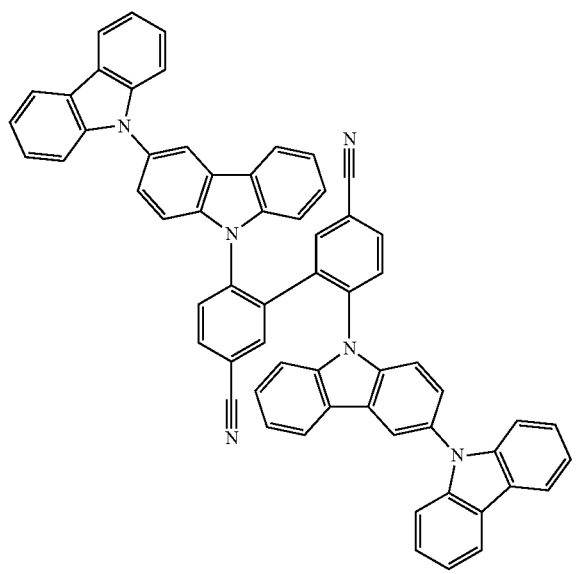

13

The film emission of 13 (10% in PMMA) was measured. The emission maximum is at 441 nm. The photoluminescence quantum yield (PLQY) is 48%. The full width at half maximum (FWHM) is 66 nm.

Example 14

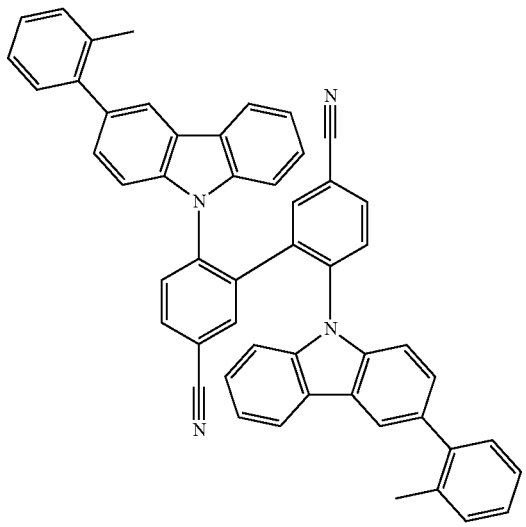

14

The film emission of 14 (10% in PMMA) was measured. The emission maximum is at 433 nm. The photoluminescence quantum yield (PLQY) is 53%. The full width at half maximum (FWHM) is 59 nm.

Example 15

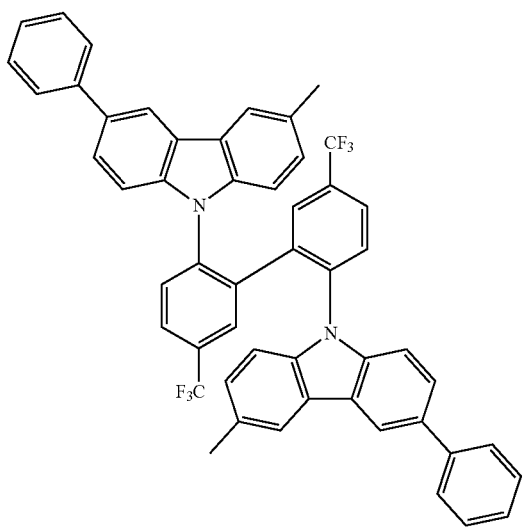

15

The film emission of 15 (10% in PMMA) was measured. The emission maximum is at 431 nm. The photoluminescence quantum yield (PLQY) is 21%. The full width at half maximum (FWHM) is 68 nm.

Example 16

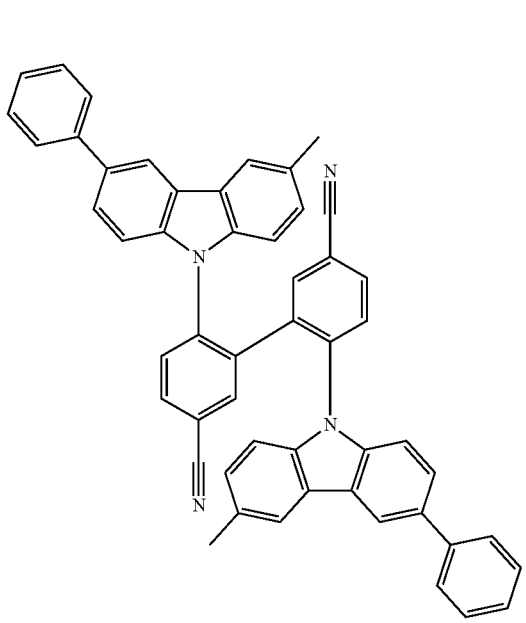

16

The film emission of 16 (10% in PMMA) was measured. The emission maximum is at 448 nm. The photoluminescence quantum yield (PLQY) is 50%. The full width at half maximum (FWHM) is 62 nm.

Example 17

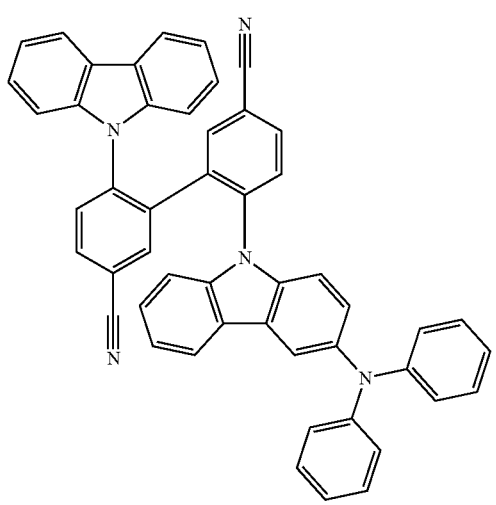

17

The film emission of 17 (10% in PMMA) was measured. The emission maximum is at 486 nm. The photoluminescence quantum yield (PLQY) is 61%. The full width at half maximum (FWHM) is 91 nm.

Example 18

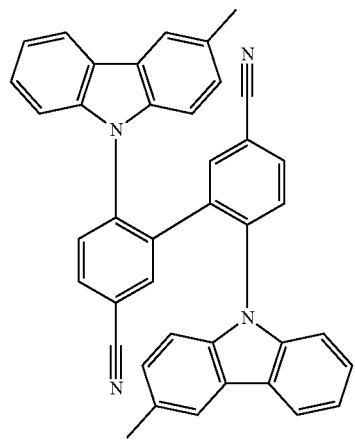

18

The film emission of 18 (10% in PMMA) was measured. The emission maximum is at 442 nm. The photoluminescence quantum yield (PLQY) is 56%. The full width at half maximum (FWHM) is 62 nm.

Example 19

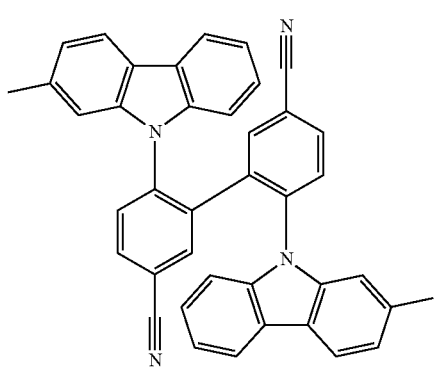

19

The film emission of 19 (10% in PMMA) was measured. The emission maximum is at 435 nm. The photoluminescence quantum yield (PLQY) is 45%. The full width at half maximum (FWHM) is 58 nm.

Example 20

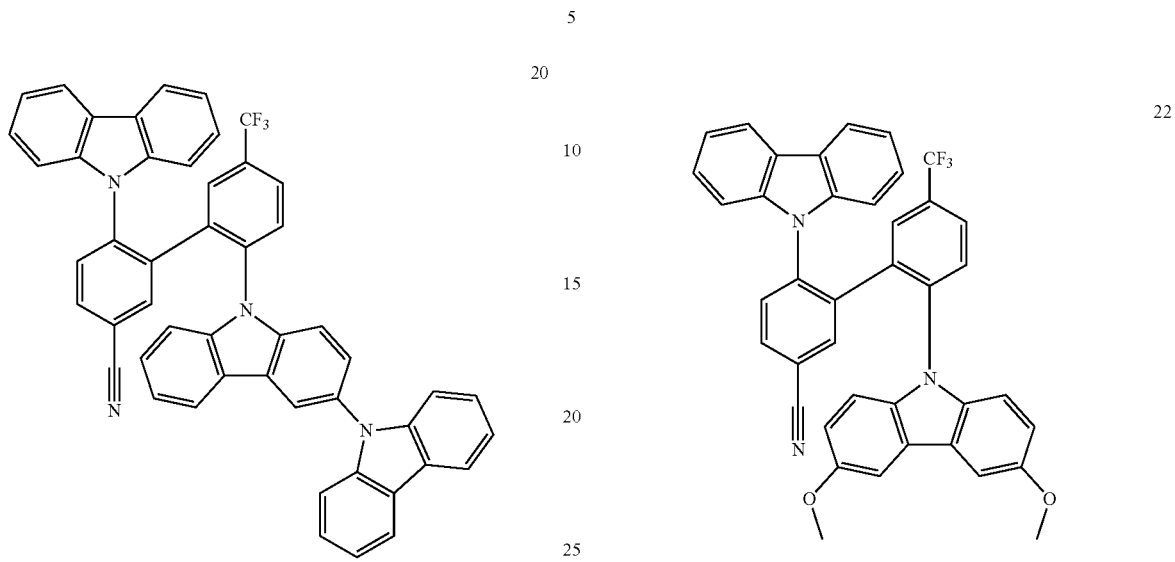

The film emission of 20 was measured. The emission maximum is at 425 nm. The photoluminescence quantum yield (PLQY) is 31%. The full width at half maximum (FWHM) is 63 nm.

Example 21

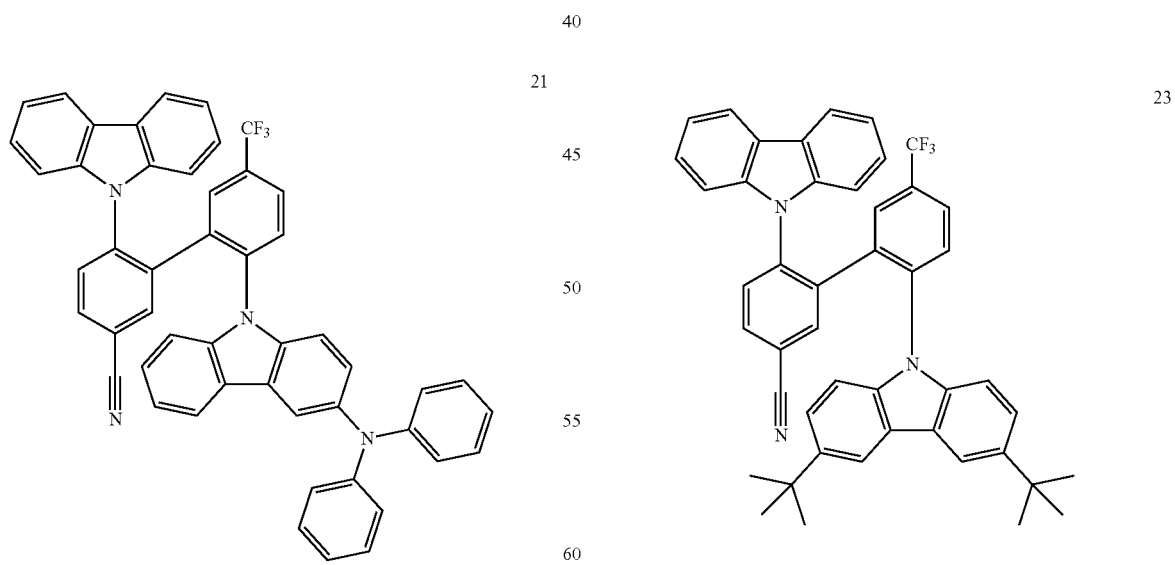

The film emission of 21 (10% in PMMA) was measured. The emission maximum is at 475 nm. The photoluminescence quantum yield (PLQY) is 39%. The full width at half maximum (FWHM) is 92 nm.

Example 22

The film emission of 22 (10% in PMMA) was measured. The emission maximum is at 459 nm. The photoluminescence quantum yield (PLQY) is 54%. The full width at half maximum (FWHM) is 74 nm.

Example 23

The film emission of 23 (10% in PMMA) was measured. The emission maximum is at 432 nm. The photoluminescence quantum yield (PLQY) is 40%. The full width at half maximum (FWHM) is 61 nm.

Example 24

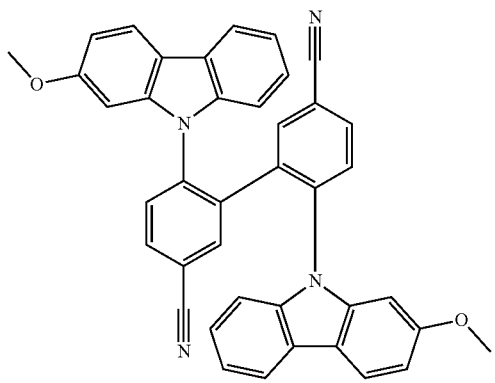

The film emission of 24 (10% in PMMA) was measured. The emission maximum is at 437 nm. The photoluminescence quantum yield (PLQY) is 52%. The full width at half maximum (FWHM) is 61 nm.

Example 25

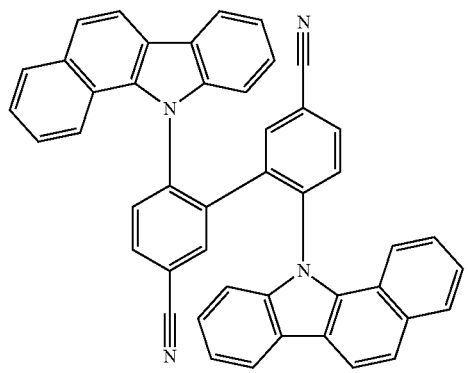

The film emission of 25 (10% in PMMA) was measured. The emission maximum is at 449 nm. The photoluminescence quantum yield (PLQY) is 25%. The full width at half maximum (FWHM) is 81 nm.

Example 26

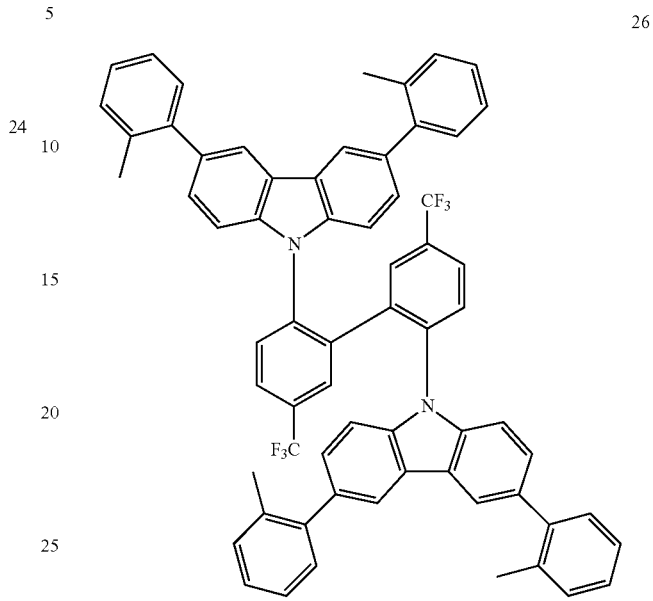

The film emission of 26 (10% in PMMA) was measured. The emission maximum is at 420 nm. The photoluminescence quantum yield (PLQY) is 22%. The full width at half maximum (FWHM) is 61 nm.

Example 27

The film emission of 27 (10% in PMMA) can be seen in FIG. 28. The emission maximum is at 435 nm. The photoluminescence quantum yield (PLQY) is 55%. The full width at half maximum (FWHM) is 58 nm.

Example 28

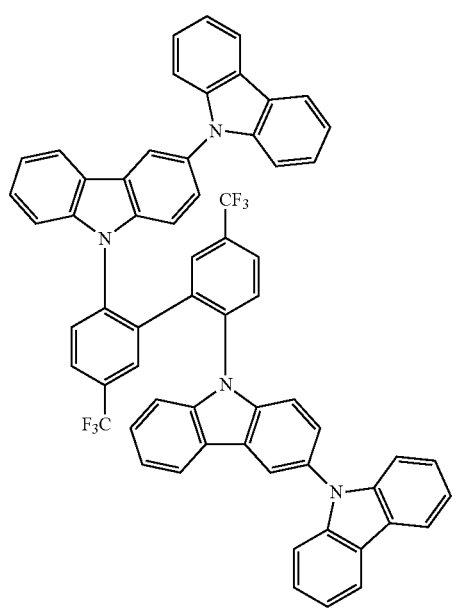

The film emission of 28 (10% in PMMA) was measured. The emission maximum is at 423 nm. The photoluminescence quantum yield (PLQY) is 20%. The full width at half maximum (FWHM) is 71 nm.

Example 29

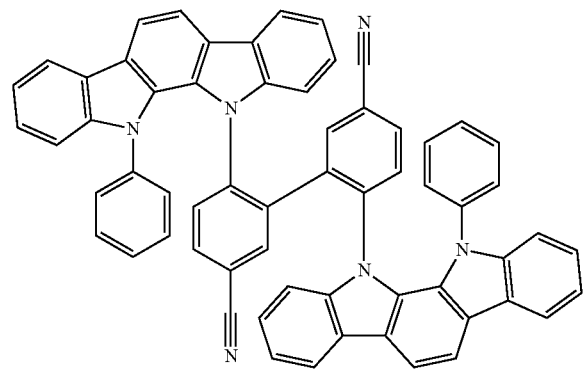

The film emission of 29 (10% in PMMA) was measured. The emission maximum is at 429 nm. The photoluminescence quantum yield (PLQY) is 42%. The full width at half maximum (FWHM) is 73 nm.

Example 30

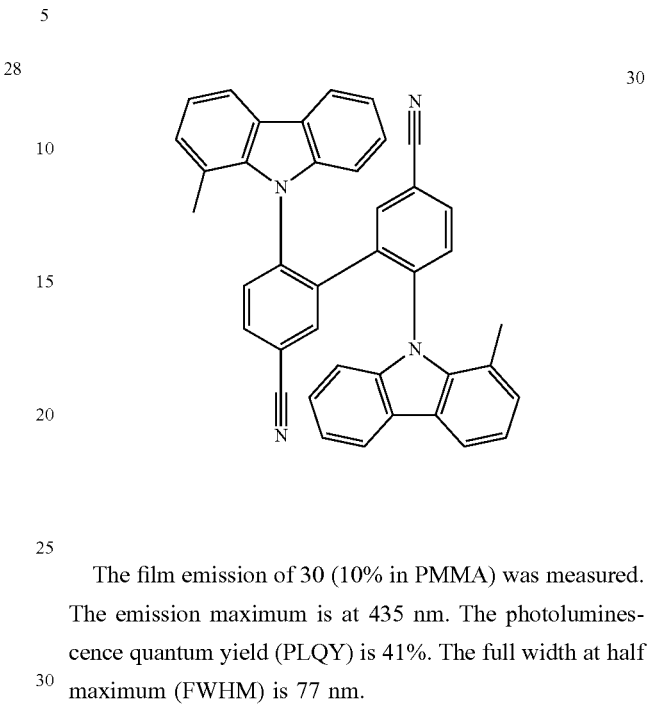

The film emission of 30 (10% in PMMA) was measured. The emission maximum is at 435 nm. The photoluminescence quantum yield (PLQY) is 41%. The full width at half maximum (FWHM) is 77 nm.

Example 31

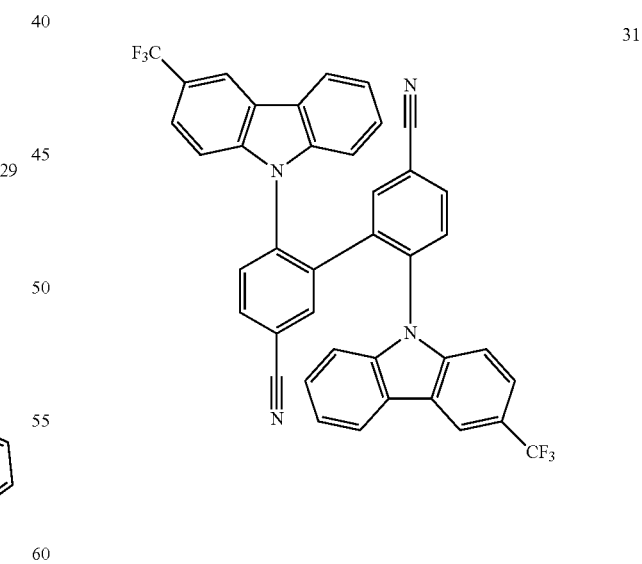

The film emission of 31 (10% in PMMA) was measured. The emission maximum is at 405 nm. The photoluminescence quantum yield (PLQY) is 33%. The full width at half maximum (FWHM) is 52 nm.

Example 32

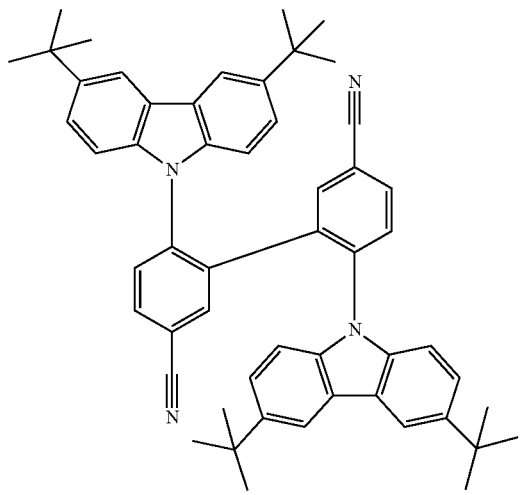

Figure 8:
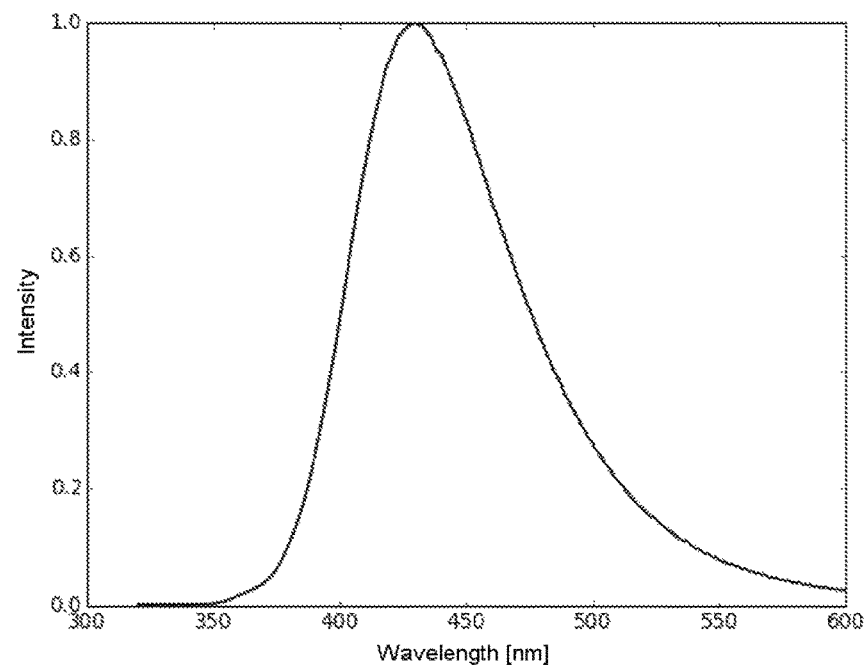
FIG. 8 is a film emission of product 32 (10% in PMMA).

The film emission of 32 (10% in PMMA) was measured (FIG. 8). The emission maximum is at 444 nm. The photoluminescence quantum yield (PLQY) is 68%. The full width at half maximum (FWHM) is 59 nm.

Molecule 5 is tested in an OLED component ("component X3") with the following construction (the fraction of the molecule of the invention in the emission layer is reported in percent by mass):

| Layer | Thickness | | |
|---|---|---|---|
| 9 | 100 nm | Al | |
| 8 | 2 nm | Liq | |
| 7 | 30 nm | TPBi | |
| 6 | 10 nm | DPEPO | |
| 5 | 20 nm | 14 (40%):DPEPO | |
| 4 | 10 nm | CzSi | |
| 3 | 20 nm | TCTA | |
| 2 | 70 nm | NPB | |
| 1 | 120 nm | ITO | |
| | | Power efficiency: | 15.6 lm/W |
| | | Current efficiency: | 20.6 cd/A |
| | | CIE: | CIEx: 0.149 |
| | | | CIEy: 0.149 |
| | | | at 14 V |
| | | External quantum yield (EQE): | 16.1% |

Further examples of organic molecules having a structure in accordance with the invention:

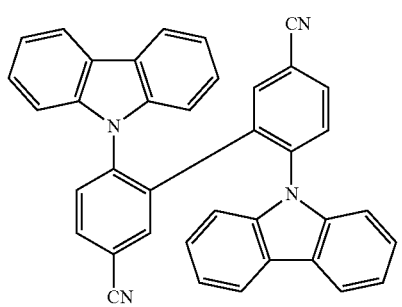

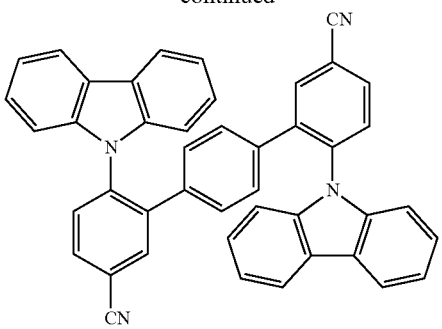

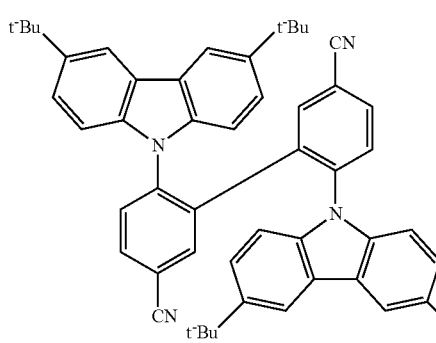

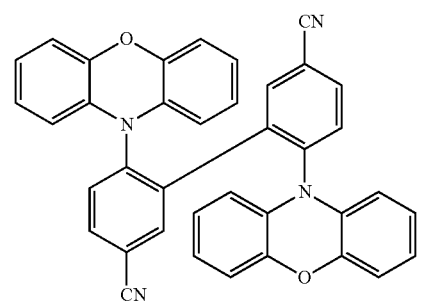

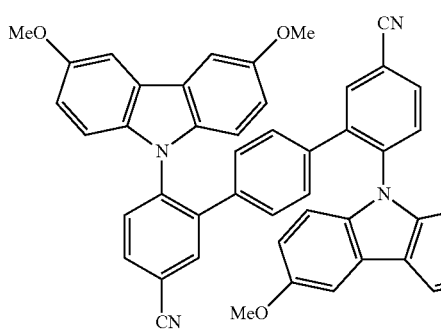

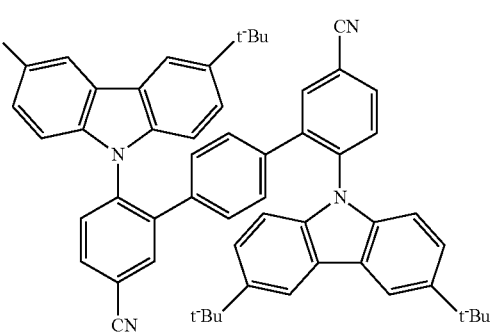

-continued
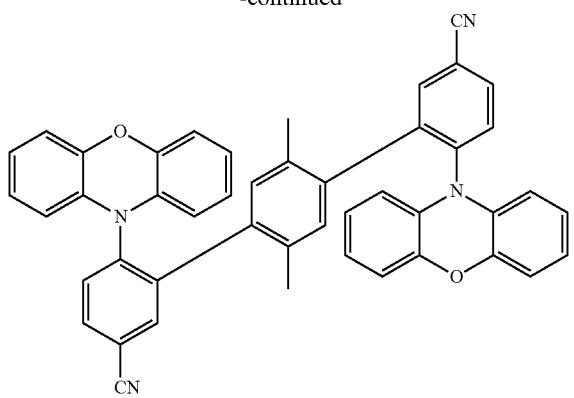
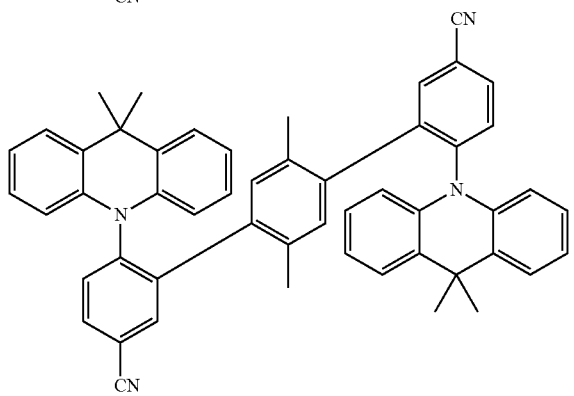
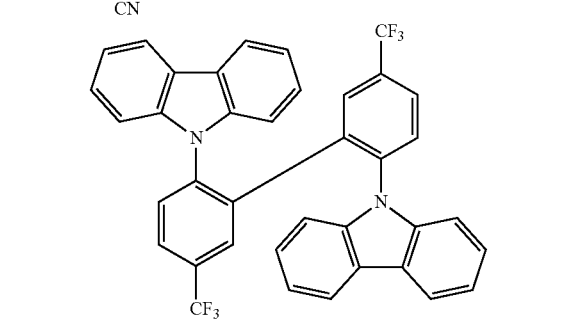
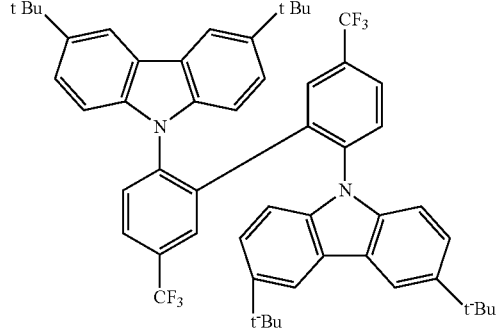
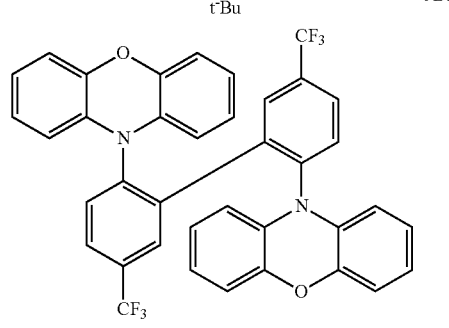
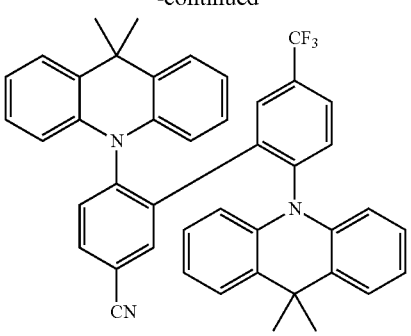
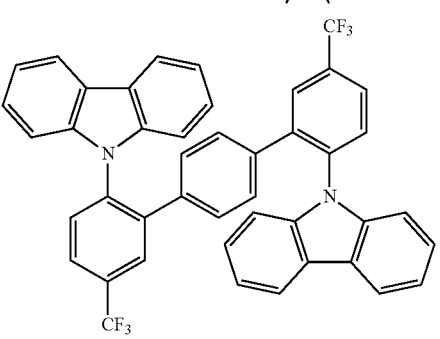
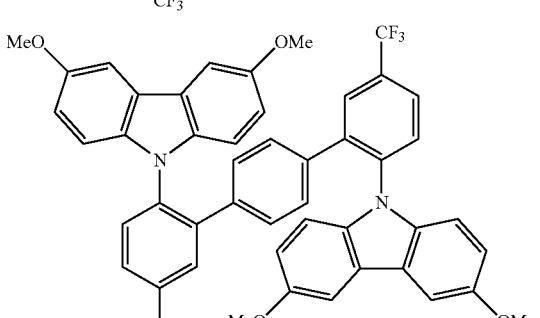
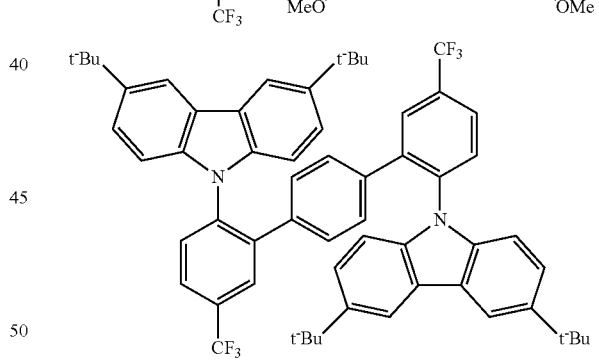
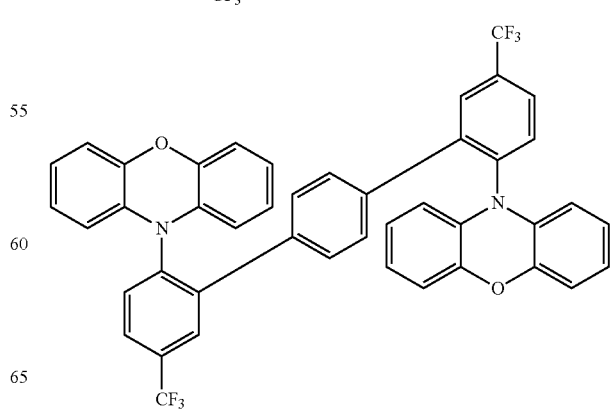

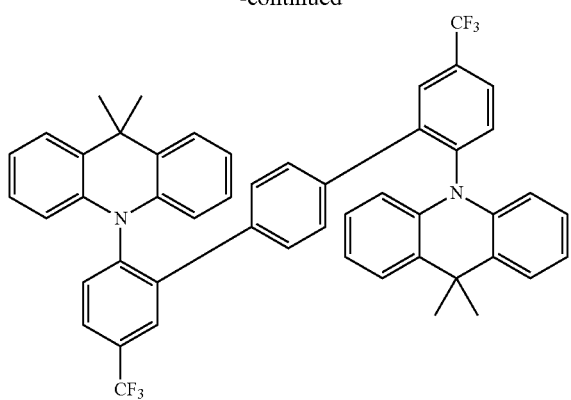
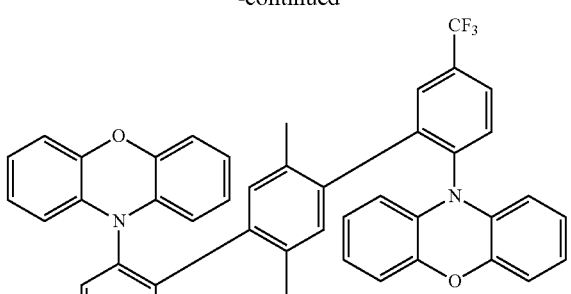
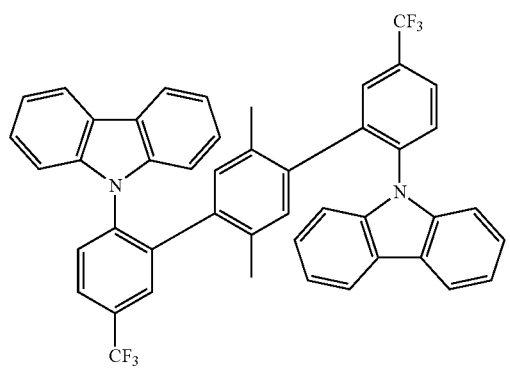
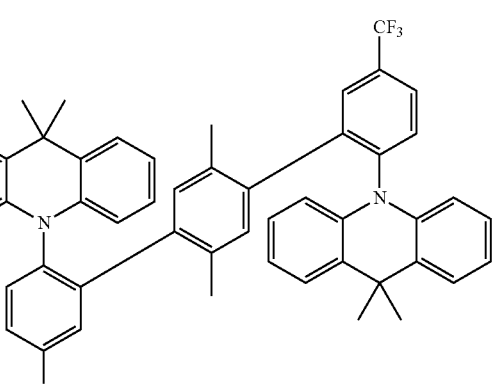
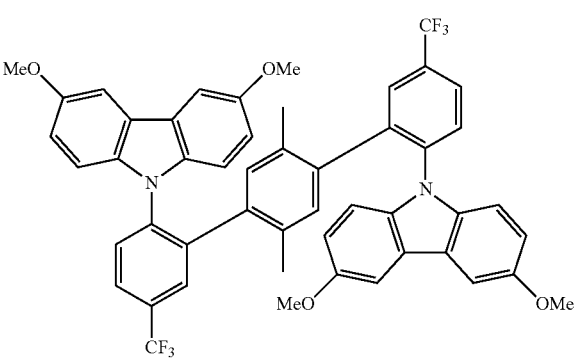
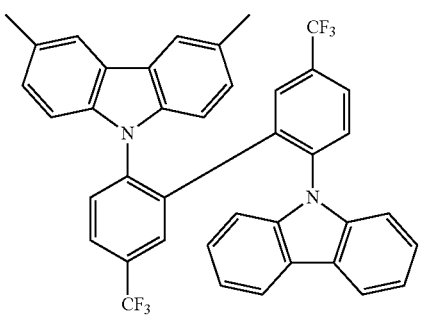
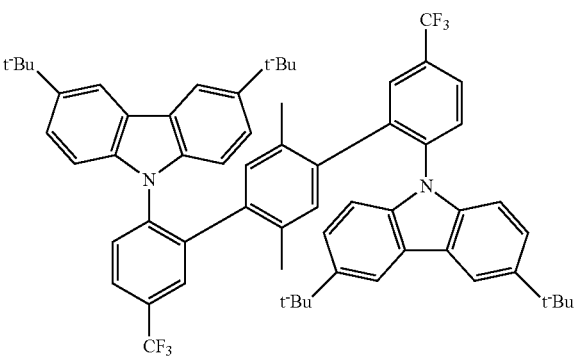
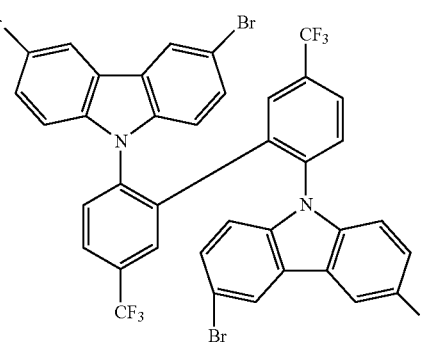

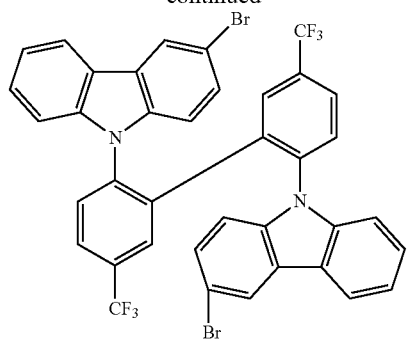
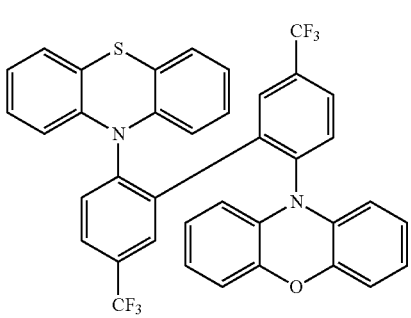
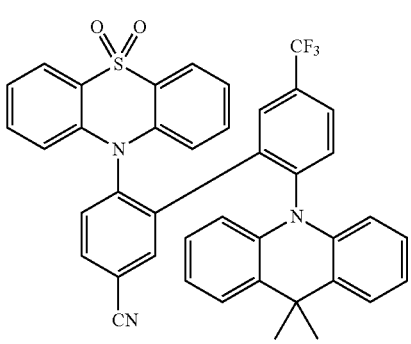
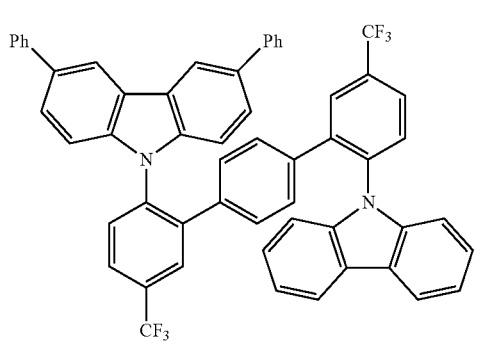
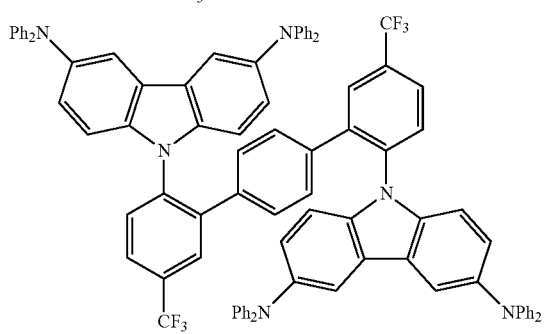

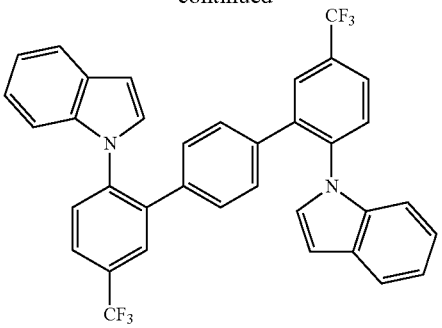
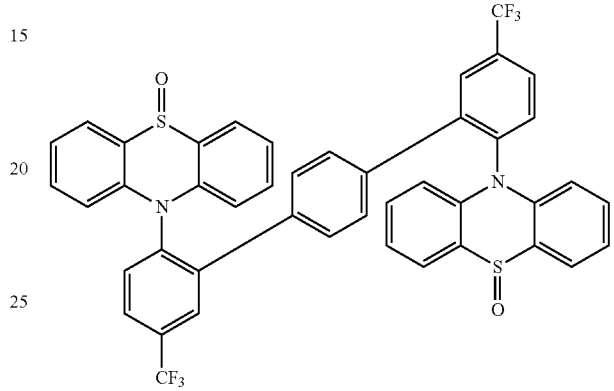
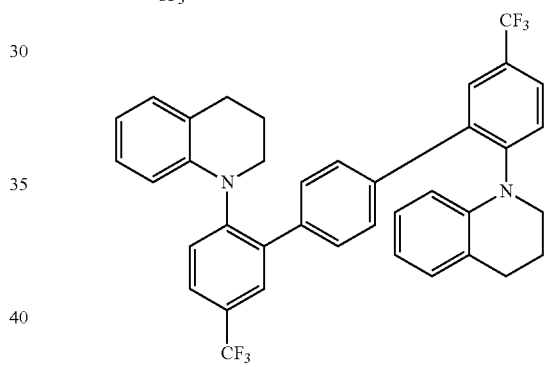

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule having two units of formula I linked to one another via a single bond or a bridge Y,

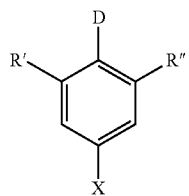

Formula I where

Y=a divalent chemical group;

X=at each occurrence independently of one another is selected from the group consisting of CN and CF$_3$;

D=a chemical unit having a structure of the formula I-1:

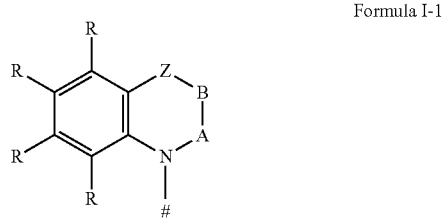

Formula I-1 wherein

=is an attachment point of the unit of formula I-1 to the structure of formula I;

A and B=independently of one another are selected from the group consisting of CRR$^1$, CR, NR, and N, with there being a single or double bond between A and B and a single or double bond between B and Z;

Z=a direct bond or a divalent organic bridge which is a substituted or unsubstituted C1-C9-alkylene, C2-C8-alkenylene, C2-C8-alkynylene or arylene group or a combination thereof, —CRR$^1$, —C═CRR$^1$, —C═NR, —NR—, —O—, —SiRR$^1$—, —S—, —S(O)—, —S(O)$_2$—, O-interrupted substituted or unsubstituted C1-C9-alkylene, C2-C8-alkenylene, C2-C8-alkynylene or arylene group, phenyl units or substituted phenyl units;

where each R and R$^1$ are identical or different at each occurrence and are H, deuterium, azide (N$_3^-$), F, Cl, Br, I, N(R$^2$)$_2$, CN, CF$_3$, NO$_2$, OH, COOH, COOR$^2$, CO(NR$^2$)$_2$, Si(R$^2$)$_3$, B(OR$^2$)$_2$, C(═O)R$^2$, P(═O)(R$^2$)$_2$, S(═O)R$^2$, S(═O)$_2$R$^2$, OSO$_2$R$^2$, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which in each case may be substituted by one or more radicals R$^2$, it being possible for one or more non-adjacent CH$_2$ groups to be replaced by R$^2$C═CR$^2$, Si(R$^2$)$_2$, Ge(R$^2$)$_2$, Sn(R$^2$)$_2$, C═O, C═S, C═Se, C═NR$^2$, P(═O)(R$^2$), SO, SO$_2$, NR$^2$, O, S or CONR$^2$, and it being possible for one or more H atoms to be replaced by deuterium, F, Cl, Br, I, CN, CF$_3$ or NO$_2$, or is an aromatic or heteroaromatic ring system having 5 to 60 aromatic ring atoms wherein this ring system is optionally substituted in each case by one or more radicals R$^2$, or is an aryloxy or heteroaryloxy group having 5 to 60 aromatic ring atoms, wherein this ring system is optionally substituted by one or more radicals R$^2$, or is a diarylamino group, diheteroarylamino group or arylheteroarylamino group having 10 to 40 aromatic ring atoms wherein this ring system is optionally substituted by one or more radicals R$^2$, or is a combination of these systems, or is a crosslinkable unit QE which may be crosslinked by acid-catalytic, thermal or UV crosslinking methods in the presence or absence of a photoinitiator or by microwave radiation; optionally two or more of these substituents R and R$^1$ may form with one another a mono- or polycyclic, aliphatic, aromatic and/or benzo-fused ring system;

R$^2$, identically or differently at each occurrence, is H, deuterium, F, Cl, Br, I, N(R$^3$)$_2$, CN, CF$_3$, NO$_2$, OH, COOH, COOR$^3$, CO(NR$^3$)$_2$, Si(R$^3$)$_3$, B(OR$^3$)$_2$, C(═O)R$^3$, P(═O)(R$^3$)$_2$, S(═O)R$^3$, S(═O)$_2$R$^3$, OSO$_2$R$^3$, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which may be substituted in each case by one or more radicals R$^3$, it being possible for one or more non-adjacent CH$_2$ groups to be replaced by R$^3$C═CR$^3$, Si(R$^3$)$_2$, Ge(R$^3$)$_2$, Sn(R$^3$)$_2$, C═O, C═S, C═Se, C═NR$^3$, P(═O)(R$^3$), SO, SO$_2$, NR$^3$, O, S or CONR$^3$, and it being possible for one or more H atoms to be replaced by deuterium, F, Cl, Br, I, CN, CF$_3$ or NO$_2$, or is an aromatic or heteroaromatic ring system having 5 to 60 aromatic ring atoms wherein this ring system is optionally substituted in each case by one or more radicals R$^3$, or is an aryloxy or heteroaryloxy group having 5 to 60 aromatic ring atoms wherein this ring system is optionally substituted by one or more radicals R$^3$, or is a diarylamino group, diheteroarylamino group or arylheteroarylamino group having 10 to 40 aromatic ring atoms wherein this ring system is optionally substituted by one or more radicals R$^3$, or is a combination of these systems; where optionally two or more of these substituents R$^2$ form with one another a mono- or polycyclic, aliphatic, aromatic and/or benzo-fused ring system;

R$^3$, identically or differently at each occurrence, is H, deuterium, F, CF$_3$ or an aliphatic, aromatic and/or heteroaromatic hydrocarbon radical having 1 to 20 C atoms, in which also one or more H atoms may be replaced by F or CF$_3$; where optionally two or more substituents R$^3$ form with one another a mono- or polycyclic, aliphatic ring system;

R'=attachment position for the second unit of the formula I or selected from the group consisting of Y, H, N(R$^4$)$_2$, OR$^4$, a linear alkyl or alkoxy group having 1 to 40 carbon atoms or a branched or cyclic alkyl or alkoxy group having 3 to 40 carbon atoms wherein this system is optionally substituted in each case by one or more radicals R$^4$, and an aromatic or heteroaromatic ring system having 5 to 60 aromatic ring atoms wherein this ring system is optionally substituted in each case by one or more radicals R$^4$;

R"=attachment position for the second unit of the formula I or selected from the group consisting of Y, N(R$^4$)$_2$, OR$^4$, a linear alkyl or alkoxy group having 1 to 40 carbon atoms or a branched or cyclic alkyl or alkoxy group having 3 to 40 carbon atoms wherein this group is optionally substituted in each case by one or more radicals R$^4$, and an aromatic or heteroaromatic ring system having 5 to 60 aromatic ring atoms wherein this ring system is optionally substituted in each case by one or more radicals R$^4$;

with the proviso that if R' is Y, R" is not Y, and, if R" is Y, R' is not Y;

and with the proviso that if R' is the attachment position for the second unit of the formula I, R" is not the attachment position for the second unit of the formula I, and, if R" is the attachment position for the second unit of the formula I, R' is not the attachment position for the second unit of the formula I;

R$^4$, identically or differently at each occurrence, is H, deuterium, N(R$^5$)$_2$, Si(R$^5$)$_3$, a linear alkyl, alkoxy or thioalkoxy group having 1 to 40 carbon atoms or a branched or cyclic alkyl, alkoxy or thioalkoxy group having 3 to 40 carbon atoms wherein this group is optionally substituted in each case by one or more radicals $R^5$, or is an aromatic or heteroaromatic ring system having 5 to 60 aromatic ring atoms wherein this ring system is optionally substituted in each case by one or more radicals $R^5$, or is an aryloxy or heteroaryloxy group having 5 to 60 aromatic ring atoms wherein this group is optionally substituted by one or more radicals $R^5$, or is a diarylamino group, diheteroarylamino group or arylheteroarylamino group having 10 to 40 aromatic ring atoms wherein this ring system is optionally substituted by one or more radicals $R^5$, or is a combination of these systems; where optionally two or more of these substituents $R^5$ may also form with one another a mono- or polycyclic, aliphatic, aromatic and/or benzo-fused ring system; and $R^5$, identically or differently at each occurrence, is H, deuterium or an aliphatic, aromatic and/or heteroaromatic hydrocarbon radical having 1 to 20 C atoms; where optionally two or more substituents $R^5$ form with one another a mono- or polycyclic, aliphatic ring system.

2. The organic molecule according to claim 1, wherein

R'=the attachment position for the second unit of the formula I or selected from the group consisting of Y, H, $N(R^4)_2$, $OR^4$, a linear alkyl or alkoxy group having 1 to 40 carbon atoms or a branched or cyclic alkyl or alkoxy group having 3 to 40 carbon atoms wherein this group is optionally substituted in each case by one or more radicals $R^4$, and an aromatic or heteroaromatic ring system having 5 to 60 aromatic ring atoms wherein this ring system is optionally substituted in each case by one or more radicals $R^4$; and R"=the attachment position for the second unit of the formula I or selected from the group consisting of Y, $N(R^4)_2$, $OR^4$, a linear alkyl or alkoxy group having 1 to 40 carbon atoms or a branched or cyclic alkyl or alkoxy group having 3 to 40 carbon atoms wherein this group is optionally to be substituted in each case by one or more radicals $R^4$, and an aromatic or heteroaromatic ring system having 5 to 60 aromatic ring atoms wherein this ring system is optionally substituted in each case by one or more radicals $R^4$;

wherein the heteroaromatic ring system is not an N-heteroaromatic;

wherein, if R' is Y, R" is not Y, and, if R" is Y, R' is not Y;

wherein if R' is the attachment position for the second unit of the formula I, then R" is not the attachment position for the second unit of the formula I, and, if R" is the attachment position for the second unit of the formula I, then R' is not the attachment position for the second unit of the formula I; and wherein Y and $R^4$ have the aforestated meanings.

3. The organic molecule according to claim 1, wherein

R'=the attachment position for the second unit of the formula I or selected from the group consisting of Y, H, $N(R^4)_2$, $OR^4$, thiophene which may be substituted by one or more radicals $R^4$, a linear alkyl or alkoxy group having 1 to 40 carbon atoms or a branched or cyclic alkyl or alkoxy group having 3 to 40 carbon atoms wherein this group is optionally substituted in each case by one or more radicals $R^4$, and an aromatic ring system having 5 to 60 aromatic ring atoms wherein this ring system is optionally substituted by one or more radicals $R^4$;

R"=the attachment position for the second unit of the formula I or selected from the group consisting of Y, $N(R^4)_2$, $OR^4$, thiophene which may be substituted by one or more radicals $R^4$, a linear alkyl or alkoxy group having 1 to 40 carbon atoms or a branched or cyclic alkyl or alkoxy group having 3 to 40 carbon atoms wherein this group is optionally substituted in each case by one or more radicals $R^4$, and an aromatic ring system having 5 to 60 aromatic ring atoms wherein this ring system is optionally substituted by one or more radicals $R^4$;

wherein if R' is Y, then R" is not Y, and, if R" is Y, then R' is not Y;

and wherein if R' is the attachment position for the second unit of the formula I, then R" is not the attachment position for the second unit of the formula I, and, if R" is the attachment position for the second unit of the formula I, then R' is not the attachment position for the second unit of the formula I;

wherein Y and $R^4$ have the aforestated meanings.

4. The organic molecule according to claim 1, wherein

R' is H and R" is the attachment point for the second unit of the formula I or is Y; wherein Y has the aforestated meaning.

5. The organic molecule according to claim 1, wherein the donor group having electron-donating properties of the formula I-1 has a structure of the formula II:

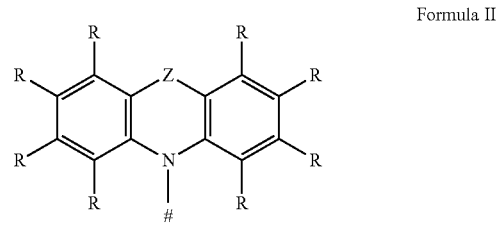

Formula II where #, Z and R have the aforestated meanings.

6. The organic molecule according to claim 1, wherein the donor group having electronic-donating properties of the formula I-1 has a structure of the formula III:

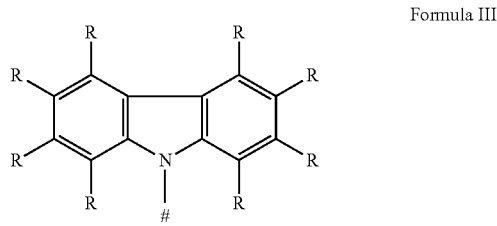

Formula III where # and R have the aforestated meanings.

7. The organic molecule according to claim 1, wherein the organic molecule has a structure of the formula XII:

Formula XII

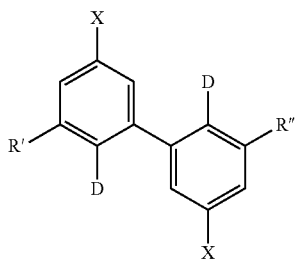

where D, R' and X have the aforestated meanings.

8. The organic molecule according to claim 7, wherein R' is H.

9. The organic molecule according to claim 1, wherein the accepting unit X of the formula I is CN.

10. The organic molecule according to claim 1, wherein the accepting unit X of the formula I is $CF_3$.

11. The organic molecule according to claim 1, wherein the bridge Y is selected from the structures of the formulae IV to X IV
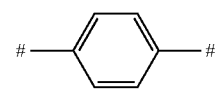

V
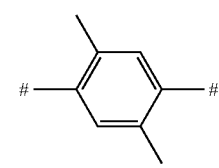

VI
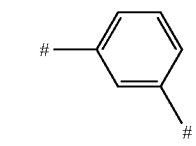

VII
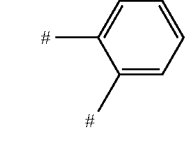

VIII
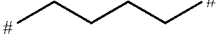

IX

X
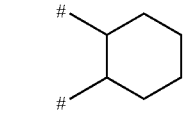

wherein

\#=the attachment point of the bridge Y to the structure of formula I.

12. The organic molecule according to claim 9, wherein the bridge Y is selected from the structures of the formulae IV to X IV

V
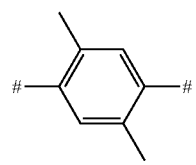

VI
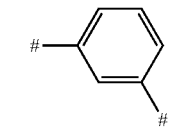

VII
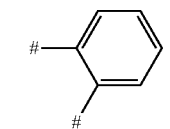

VIII
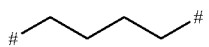

IX

X
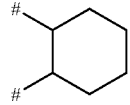

wherein

\#=the attachment point of the bridge Y to the structure of formula I.

13. The organic molecule according to claim 10, wherein the bridge Y is selected from the structures of the formulae IV to X IV
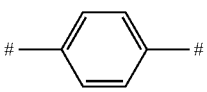

V
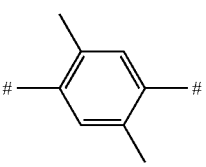

VI
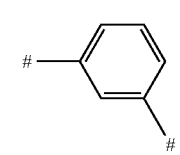

VII
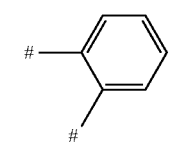

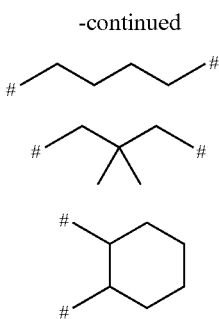

wherein
\#=the attachment point of the bridge Y to the structure of formula I.

14. A process for preparing an organic molecule according to claim 1, comprising coupling one unit of formula I to another unit of formula I.

15. An optoelectronic device comprising an organic molecule according to claim 1.

16. The optoelectronic device according to claim 15, wherein the optoelectronic device is an organic light-emitting diode, light-emitting electrochemical cell, organic light-emitting sensor, an organic diode, an organic solar cell, an organic transistor, an organic field-effect transistor, an organic laser or a down-conversion element.

17. The optoelectronic device according to claim 15, wherein the organic molecule is one of an emitter and an absorber in the optoelectronic component.

18. The optoelectronic device according to claim 15, wherein the proportion of the organic molecule in the emitter or absorber is in the range of 1% to 99%.

19. The optoelectronic device according to claim 16, comprising
a substrate,
an anode and
a cathode, wherein the anode or the cathode is applied to the substrate, and at least one light-emitting layer is disposed between anode and cathode and which comprises the organic molecule according to claim 1.

20. A process for producing an optoelectronic component, comprising processing of the organic molecule according to claim 1 by a vacuum vaporization process or from a solution.

* * * * *

UNITED STATES PATENT AND TRADEMARK OFFICE
CERTIFICATE OF CORRECTION

PATENT NO. : 10,263,196 B2
APPLICATION NO. : 15/541590
DATED : April 16, 2019
INVENTOR(S) : Michael Danz et al.

It is certified that error appears in the above-identified patent and that said Letters Patent is hereby corrected as shown below:

In the Claims

Column 48, Lines 11 and 12, in Claim 1, please insert --C=C,-- after "$R^3C=Cr^3$,".

Signed and Sealed this
Second Day of July, 2019

Andrei Iancu
*Director of the United States Patent and Trademark Office*